(12) United States Patent
Shimamura et al.

(10) Patent No.: US 8,784,684 B2
(45) Date of Patent: Jul. 22, 2014

(54) POLYMERIZABLE COMPOUND, POLYMERIZABLE LIQUID CRYSTALLINE COMPOSITION, MACROMOLECULAR COMPOUND AND FILM

(71) Applicant: FUJIFILM Corporation, Tokyo (JP)

(72) Inventors: Satoshi Shimamura, Ashigarakami-gun (JP); Mitsuyoshi Ichihashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/961,014

(22) Filed: Aug. 7, 2013

(65) Prior Publication Data

US 2013/0320260 A1   Dec. 5, 2013

Related U.S. Application Data

(63) Continuation of application No. PCT/JP2012/056502, filed on Mar. 14, 2012.

(30) Foreign Application Priority Data

Mar. 16, 2011   (JP) ................................ 2011-058442

(51) Int. Cl.
| | | |
|---|---|---|
| C09K 19/34 | (2006.01) | |
| C09K 19/32 | (2006.01) | |
| C09K 19/06 | (2006.01) | |
| C09K 19/52 | (2006.01) | |
| C09K 19/00 | (2006.01) | |
| C08F 2/00 | (2006.01) | |
| C08F 26/06 | (2006.01) | |
| C08F 126/06 | (2006.01) | |
| C08F 226/06 | (2006.01) | |
| C07D 265/00 | (2006.01) | |
| C07D 265/12 | (2006.01) | |
| C07D 498/00 | (2006.01) | |

(52) U.S. Cl.
USPC .............. 252/299.61; 252/299.1; 252/299.6; 252/299.62; 428/1.1; 428/1.3; 526/72; 526/258; 526/259; 544/92; 544/63; 544/88; 544/89; 544/90

(58) Field of Classification Search
USPC .............. 252/299.01, 299.6, 299.61, 299.62; 428/1.1, 1.3; 526/72, 258, 259; 544/1, 544/63, 88, 89, 90, 92
See application file for complete search history.

(56) References Cited

U.S. PATENT DOCUMENTS

| | | | |
|---|---|---|---|
| 2009/0239982 A1* | 9/2009 | Amasaki et al. | ................ 524/92 |
| 2011/0024701 A1* | 2/2011 | Furukawa et al. | ............ 252/589 |

FOREIGN PATENT DOCUMENTS

| | | |
|---|---|---|
| JP | 57-92312 A | 6/1982 |
| JP | 2007-206461 A | 8/2007 |
| JP | 2007-279363 A | 10/2007 |
| JP | 2008-203709 A | 9/2008 |
| JP | 2009-149754 A | 7/2009 |
| WO | WO 2010/095602 A1 | 8/2010 |

OTHER PUBLICATIONS

Broer et al., "Photo-Induced Diffusion in Polymerizing Chiral-Nematic Media," Advanced Materials, 1999, vol. 11, No. 7, pp. 573-578.
International Search Report issued in PCT/JP2012/056502, mailed on May 22, 2012.
Written Opinion issued in PCT/JP2012/056502, mailed on May 22, 2012.
Forms PCT/IB/338, PCT/IB/373, PCT/ISA/237 (with English translation), and PCT/IB/326, mailed Sep. 26, 2013, for International Application No. PCT/JP2012/056502.

* cited by examiner

*Primary Examiner* — Geraldina Visconti
(74) *Attorney, Agent, or Firm* — Birch, Stewart, Kolasch & Birch, LLP

(57) ABSTRACT

A compound which has a benzoxazinone ring and an aromatic ring that directly bonds to the benzoxazinone ring, and has a mesogenic core substituted by a substituent having a polymerizable functional group is excellent in terms of durability, colorless, and exhibits a high Δn while having an azomethine bond.

19 Claims, 1 Drawing Sheet

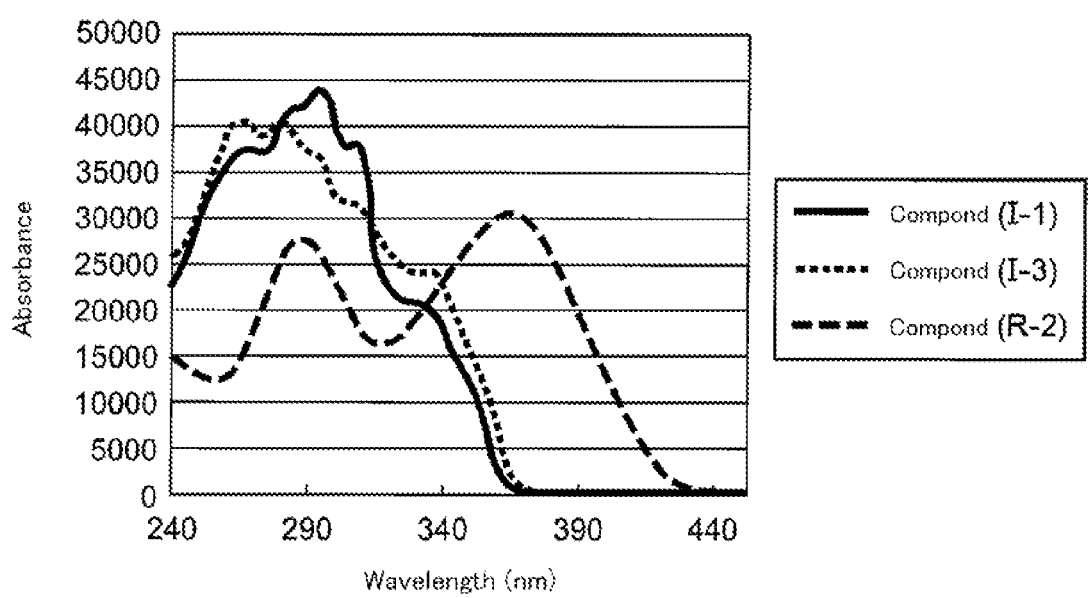

POLYMERIZABLE COMPOUND, POLYMERIZABLE LIQUID CRYSTALLINE COMPOSITION, MACROMOLECULAR COMPOUND AND FILM

CROSS-REFERENCE TO RELATED APPLICATIONS

This application is a continuation application of International Application No. PCT/JP2012/056502, filed Mar. 14, 2012, which in turn claims the benefit of priority from Japanese Application No. 2011-058442, filed Mar. 16, 2011, the disclosures of which applications are incorporated by reference herein in their entirety.

BACKGROUND OF THE INVENTION

1. Field of the Invention

The present invention relates to a polymerizable compound useful for a variety of uses including materials of a variety of optical members, such as optically anisotropic films and heat shielding films. In addition, the invention relates to a polymerizable liquid crystalline composition, a macromolecular compound and a film for which the polymerizable compound is used.

2. Description of the Related Art

In recent years, there has been a demand for a decrease in the size of a liquid crystal display apparatus, and, accordingly, there has been a demand for a decrease in the thickness of an optical film. For example, it is possible to decrease the film thickness by using a liquid crystal exhibiting a high Δn as an optical film such as a wave plate. Δn is one of the important basic physical properties of a liquid crystalline compound, and a liquid crystal exhibiting a high Δn can be used in many industrial fields, such as a wave plate, a polarization element, a selective reflection film, a color filter, an antireflection film, a viewing angle compensation film, holography and an oriented film which are components of an optical element (Non-Patent Literature 1).

In the past, a variety of compounds having an azomethine bond were proposed as a polymerizable liquid crystalline compound having a high Δn (Patent Literatures 1 to 4). All of the compounds described in the above patent literatures have a structure represented by -Ph$^1$-CH=N-Ph$^2$- [here, Ph$^1$ and Ph$^2$ represent a 1,4-phenylene group] in the molecule, and other structural examples are not described.

CITATION LIST

[Patent Literature 1] JP-A-2007-279363
[Patent Literature 2] JP-A-2007-206461
[Patent Literature 3] JP-A-2009-149754
[Patent Literature 4] JP-A-2008-203709
[Non-Patent Literature 1] D. J. Broer, G. N. Mol, J. A. M. M. Van Haaren, and J. Lub Adv. Mater., 1999, 11, 573

SUMMARY OF THE INVENTION

In order to make a polymerizable liquid crystal have a high Δn, it is effective for a compound to absorb light at a long wavelength. However, when the compound absorbs light at an excessively long wavelength, there is a problem in that the compound is colored, and therefore, in the case of use in which the compound needs to be colorless, it becomes important to make the compound absorb light in a range of long wavelengths in which the compound is not colored and to achieve a high Δn. In well-known polymerizable azomethine liquid crystalline compounds of the related art, there was a problem in that Δn was not sufficient or, even when a high Δn was achieved, the compound absorbed light at a long wavelength such that the compound was colored. In addition, there was a problem in that the azomethine bond was easily hydrolyzed and an aniline compound generated from the hydrolysis was further oxidized so as to generate a colored substance, and it was difficult to expand the use of the compound to use in which the compound needs to be colorless in terms of durability.

The invention has been made to solve the above problems of the related art. That is, an object is to provide a new colorless polymerizable compound which exhibits a high Δn, has an azomethine bond and is excellent in terms of durability.

As a result of repeating thorough studies in order to solve the above problems, the present inventors found that a polymerizable compound having a specific structure including a benzoxazinone ring exhibits a high Δn, is colorless and excellent in terms of durability, and provided the invention. Means for achieving the object is as follows.

[1] A compound which has a benzoxazinone ring and an aromatic ring that directly bonds to the benzoxazinone ring, and has a mesogenic core substituted by a substituent having a polymerizable functional group.

[2] A compound represented by the following formula (I).

Formula (I)

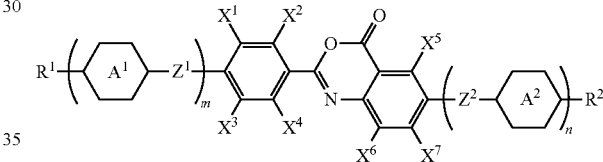

[In the formula (I), each of R$^1$ and R$^2$ independently represents a hydrogen atom, a halogen, NO$_2$, CN, NCS, a linear, branched or cyclic alkyl group having 1 to 12 carbon atoms (here, among —CH$_2$— that configure the alkyl group, one —CH$_2$— or two or more non-adjacent —CH$_2$— may be substituted by —O—, —S—, —CO—, —COO—, —OCO—, —OCOO—, —CH=CH—, —C≡C—, —CONR$^3$—, —NR$^3$CO— or —NR$^3$—) or P-Sp-L-, and at least one of R$^1$ and R$^2$ is P-Sp-L-;

P represents a polymerizable functional group;

Sp represents a single bond or an alkylene group having 1 to 12 carbon atoms (here, among non-terminal —CH$_2$— that configure the alkylene group, one non-terminal —CH$_2$— or two or more non-adjacent non-terminal —CH$_2$— may be substituted by —O—, —S—, —CO—, —COO—, —OCO—, —CH=CH—, —C≡C—, —CONR$^4$—, —NR$^4$CO— or —NR$^4$—);

L represents —O—, —S—, —CO—, —COO—, —OCO—, —OCOO—, —CONR$^5$—, —NR$^5$CO—, —NR$^5$— or a single bond; when Sp is a single bond, L is also a single bond;

each of A$^1$ and A$^2$ independently represents a 1,4-phenylene group; one or two or more hydrogen atoms in the 1,4-phenylene group may be substituted by an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $Z^1$ and $Z^2$ independently represents —COO—, —OCO—, —CONR$^6$—, —NR$^6$CO—, —OCH$_2$—, —CH$_2$O—, —CH$_2$S—, —SCH$_2$—, —CH$_2$CH$_2$— or a single bond;

each of $X^1$, $X^2$, $X^3$, $X^4$, $X^5$, $X^6$ and $X^7$ independently represents a hydrogen atom, an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $R^3$, $R^4$, $R^5$ and $R^6$ independently represents a hydrogen atom or an alkyl group having 1 to 4 carbon atoms;

each of m and n independently represents 0, 1 or 2, and m+n=1 or 2.]

[3] The compound according to [2], in which, in the formula (I), when m=n=1, $Z^1$ is —COO—, and $Z^2$ is —OCO—.

[4] The compound according to [3], in which, in the formula (I), $X^3$ is a hydrogen atom or a methoxy group.

[5] The compound according to [2], in which, in the formula (I), when m=0 and n=1, $Z^2$ is —OCO—.

[6] The compound according to [2], in which, in the formula (I), when m=1 and n=0, $Z^1$ is —COO—.

[7] The compound according to any one of [1] to [6], in which, in the formula (I), P is a polymerizable functional group selected from a group consisting of groups represented by the following formulae (P-1) to (P-5).

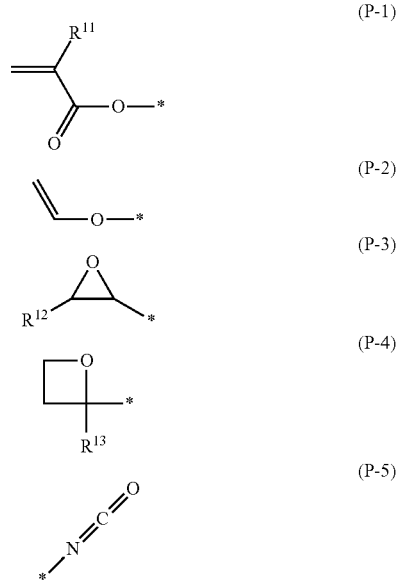

[In the formulae, each of $R^{11}$ to $R^{13}$ independently represents a hydrogen atom or a methyl group.]

[8] The compound according to any one of [1] to [7], in which, in the formula (I), P is a methacrylate group or an acrylate group.

[9] The compound according to any one of [1] to [8], in which, in the formula (I), Sp is an alkylene group having 2 to 8 carbon atoms.

[10] The compound according to any one of [1] to [9], in which, in the formula (I), $R^1$ and $R^2$ are a group represented by P-Sp-L-.

[11] A polymerizable liquid crystalline composition containing the compound according to any one of [1] to [10] and a chiral agent.

[12] A macromolecular compound obtained by polymerizing the compound according to any one of [1] to [10].

[13] A film using the compound according to any one of [1] to [10].

The compound and the film of the invention exhibit effects of being colorless, exhibiting a high Δn and being excellent in terms of durability.

BRIEF DESCRIPTION OF THE DRAWING

FIG. 1 illustrates absorption spectrum curves of Compound (I-1) and Compound (I-3) of the invention and Comparative Compound (R-2).

MODE FOR CARRYING OUT THE INVENTION

Hereinafter, the invention will be described in detail. Configuration requirements described below will be described based on typical embodiments or specific examples of the invention, but the invention is not limited to the above embodiments or specific examples. Meanwhile, numeric ranges expressed using "to" in the present specification include numeric values before and after "to" as the lower limit value and the upper limit value.

1. The Compound of the Invention

The compound of the invention is a compound which has a benzoxazinone ring and an aromatic ring that directly bonds to the benzoxazinone ring, and has a mesogenic core substituted by a substituent having a polymerizable functional group. A liquid crystalline compound of the related art having an azomethine group in the molecule exhibits a high Δn, but has a problem of coloring or durability, and is thus used in a limited range. In contrast to the compound of the related art, the compound of the invention exhibits a sufficiently high Δn and is white, which does not cause a problem of coloring. Furthermore, the compound of the invention is also favorable in terms of solubility in a solvent and compatibility with other liquid crystalline materials, and is curable through polymerization so as to be useful in a variety of uses, such as optical members. Particularly, due to the high Δn, the compound is useful in producing an optical film, such as a phase difference film and a selective reflection film, which are required to exhibit desired optical characteristics in a thin film form.

In the compound of the invention, when the chain length of a linking group that connects the polymerizable functional group at the terminal and the mesogenic core is extended to a certain extent, it is also possible to widen the temperature range in which the compound becomes a liquid crystalline phase so as to prevent the compound from being crystallized and whitened in a polymerization step. The number of atoms that configure a linking chain in the linking group is preferably 1 to 12, more preferably 2 to 8, and still more preferably 3 to 6. In addition, the linking group is preferably an alkylene group.

The mesogenic core in the compound of the invention is preferably a phenylene group, and more preferably a 1,4-phenylene group. In addition, the substituent including the mesogenic core may be bonded to the benzoxazinone ring, or may be bonded to the aromatic ring that directly bonds to the benzoxazinone ring. In addition, the substituent may be bonded respectively to the benzoxazinone ring and the aromatic ring that directly bonds to the benzoxazinone ring.

Hereinafter, among the compounds of the invention, particularly, the compound represented by the formula (I) will be described in detail.

Formula (I)

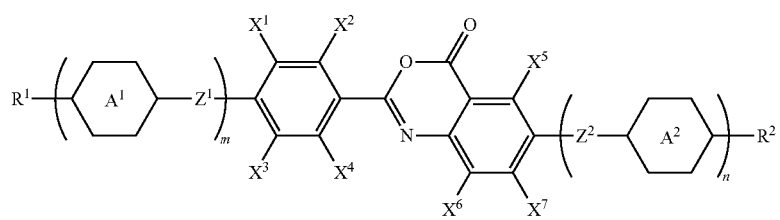

each of $R^1$ and $R^2$ in the formula (I) independently represents a hydrogen atom, a halogen, $NO_2$, CN, NCS, a linear, branched or cyclic alkyl group having 1 to 12 carbon atoms (here, among —$CH_2$— that configure the alkyl group, one —$CH_2$— or two or more non-adjacent —$CH_2$— may be substituted by —O—, —S—, —CO—, —COO—, —OCO—, —OCOO—, —CH=CH—, —C≡C—, —$CONR^3$—, —$NR^3CO$— or —$NR^3$—, and $R^3$ represents a hydrogen atom or an alkyl group having 1 to 4 carbon atoms) or P-Sp-L-, and at least one of $R^1$ and $R^2$ is P-Sp-L-. $R^1$ and $R^2$ are more preferably a linear, branched or cyclic alkyl group having 1 to 12 carbon atoms in which one $CH_2$ or two or more non-adjacent $CH_2$ may be substituted by —O— or —OCOO—, or P-Sp-L-, and still more preferably a polymerizable functional group represented by P-Sp-L-.

P in P-Sp-L- that can be $R^1$ and $R^2$ represents a polymerizable functional group. The polymerizable functional group mentioned herein conceptually includes both a group composed of only a group that directly participates in polymerization (for example, $CH_2$=CH—) and a group composed of a group that directly participates in polymerization (for example, $CH_2$=CH—) and a functional group that is bonded to the above group (for example, —CO—, —CO—O—, —O—). The polymerizable functional group is preferably a polymerizable functional group that can be radically polymerized or cationically polymerized. As the radically polymerizable functional group, a generally known radically polymerizable functional group can be used, and preferable examples thereof include (meth)acrylate groups (used as a terminology that includes both an acrylate group and a methacrylate group). In this case, it is known that, generally, the acrylate group has a faster polymerization speed, and the acrylate group is preferable from the viewpoint of improving the productivity, but the methacrylate group can be also used in the same manner as the polymerizable functional group of a liquid crystal having a high Δn. As the cationically polymerizable functional group, a generally known cationically polymerizable functional group can be used, and specific examples thereof include an alicyclic ether group, a cyclic acetal group, a cyclic lactone group, a cyclic thioether group, a spiro ortho ester group, a vinyloxy group and the like. Among the above, the alicyclic ether group and the vinyloxy group are preferable, and an epoxy group, an oxetanyl group and a vinyloxy group are particularly preferable.

P is preferably a polymerizable functional group represented by any one of the following formulae (P-1) to (P-5).

(P-1)

-continued

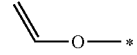
(P-2)

(P-3)

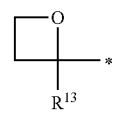
(P-4)

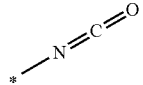
(P-5)

In the formulae, each of $R^{11}$ to $R^{13}$ independently represents a hydrogen atom or a methyl group. * represents a bonding location with Sp. P is preferably a (meth)acrylate group, that is, preferably either one of the following groups.

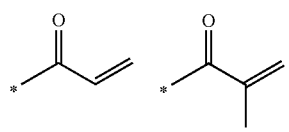

Sp in P-Sp-L- that can be $R^1$ and $R^2$ represents a single bond or an alkylene group having 1 to 12 carbon atoms (here, among non-terminal —$CH_2$— that configure the alkylene group, one non-terminal —$CH_2$— or two or more non-adjacent non-terminal —$CH_2$— may be substituted by —O—, —S—, —CO—, —COO—, —OCO—, —CH=CH—, —C≡C—, —$CONR^4$—, —$NR^4CO$— or —$NR^4$—, and $R^4$ represents a hydrogen atom or an alkyl group having 1 to 4 carbon atoms).

When the length of a side chain of the compound of the formula (I) is short (for example, the number of carbon atoms is 1 to 3), the upper temperature limit at which a liquid crystalline phase appears is high, but the compound is easily crystallized so that the solubility decreases. Therefore, there are cases in which it is necessary to decrease the fraction of the compound from the viewpoint of solubility into or compatibility with other components (for example, a solvent or other liquid crystalline materials) included in the composition. On the other hand, when the side chain is long (for example, the number of carbon atoms is 4 to 6), the solubility becomes favorable, but the upper temperature limit at which a liquid crystalline phase appears decreases, a smectic phase easily appears, or a nematic phase range is narrowed such that there are cases in which the uniformity of orientation degrades. In addition, when the side chain becomes long, since the degree of freedom of the movement of molecules increases, for use in which a highly stiff film quality is required, a compound having a short side chain is preferably used, and, for use for improving the brittleness of a film, a compound having a long side chain is preferably used. In order to satisfy the above physical properties in a favorable balance, Sp in the compound of the formula (I) is preferably an alkylene group having 2 to 8 carbon atoms, and more preferably an alkylene group having 3 to 6 carbon atoms.

L in P-Sp-L- that can be $R^1$ and $R^2$ represents —O—, —S—, —CO—, —COO—, —OCO—, —OCOO—, —CONR$^5$—, —NR$^5$CO—, —NR$^5$— or a single bond ($R^5$ represents a hydrogen atom or an alkyl group having 1 to 4 carbon atoms). L is preferably —O—, —S—, —COO—, —OCO— or —OCOO—, and more preferably —O— or —OCOO—. When Sp is a single bond, L is also a single bond.

Each of $A^1$ and $A^2$ in the formula (I) independently represents a 1,4-phenylene group. One or two or more hydrogen atoms in the 1,4-phenylene group represented by $A^1$ and $A^2$ may be substituted by an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom.

Each of $Z^1$ and $Z^2$ in the formula (I) independently represents —COO—, —OCO—, —CONR$^6$—, —NR$^6$CO—, —OCH$_2$—, —CH$_2$O—, —CH$_2$S—, —SCH$_2$—, —CH$_2$CH$_2$— or a single bond ($R^6$ represents a hydrogen atom or an alkyl group having 1 to 4 carbon atoms). As the linking group that links a ring structure, a linking group having a rigid structure is preferably used in order to stabilize the liquid crystalline phase (to improve the NI point). However, when a rigid linking group is used to a large extent, a decrease in the solubility due to the improvement of crystallinity and the contraction of the nematic liquid crystalline phase range due to the stabilization of the smectic phase can be considered. However, a single bond that supplies a rigid structure is not preferable as a linking group with a skeleton having an azomethine bond since there is a concern that light may be absorbed at a long wavelength due to expansion of π-conjugation and the compound may be colored. Therefore, $Z^1$ and $Z^2$ are selected from the above range, and are preferably —COO— or —OCO—.

Each of $X^1$, $X^2$, $X^3$, $X^4$, $X^5$, $X^6$ and $X^7$ in the formula (I) independently represents a hydrogen atom, an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom.

In order to improve the solubility of the compound, it is effective to introduce a substituent into the aromatic ring. Even in the compound represented by the formula (I), as the size of the atom in the substituent represented by $X^1$, $X^2$, $X^3$, $X^4$, $X^5$, $X^6$ and $X^7$ increases, a larger contribution is made to improve the solubility, and, as the size decreases, the solubility degrades. When handling in a manufacturing step is taken into account, the aromatic ring desirably includes a substituent. As the number of the substituents increases, an increase in the solubility can be expected; however, when there are too many substituents, the crystallinity is impaired, and therefore the compound represented by the formula (I) preferably includes 0, 1 or 2 substituents in addition to the hydrogen atom, and more preferably includes 1 substituent. In addition, a substituent that satisfies both solubility and liquid crystallinity is preferably an alkyl group having 1 to 2 carbon atoms, an alkoxy group having 1 to 2 carbon atoms or a halogen atom, and more preferably a methyl group, a methoxy group or a chlorine atom.

Each of m and n in the formula (I) independently represents 0, 1 or 2.

In order to have a high Δn, it is necessary to increase the orientation order, and, in order to increase the orientation order, it is effective to increase the upper temperature limit of the liquid crystalline phase. The compound represented by the formula (I) is a compound in which at least 3 or 4 rings of cyclic aromatic groups are linked, which has a high NI point (the transition temperature from the nematic liquid crystalline phase to an isotropic phase), specifically, exhibits an extremely high NI point of 160° C. or higher, and significantly contributes to the improvement of Δn of the composition. In addition, since the aromatic ring increases the polarizability in the long axis direction of the molecule compared with an unsaturated ring or a non-aromatic ring, and contributes to the improvement of Δn, $A^1$ and $A^2$ are limited to the 1,4-phenylene group as described above. However, an increase in the number of the rings leads to an increase in the melting point or viscosity, and there is another disadvantage that, in a use range in which the compound is used in an optical film, the compound is easily crystallized in a coating step, and the film uniformity degrades. In addition, since the solubility degrades as the number of the rings increases and handling in the manufacturing step becomes difficult, regarding the number of the rings in the compound, the number of the aromatic rings is preferably 3 or 4. Therefore, m+n in the compound of the formula (I) is 1 or 2.

When m and n in the formula (I) are both 1, a compound in which $Z^1$ is —COO— and $Z^2$ is —OCO— can be included in a preferable range.

In addition, a compound in which $X^3$ in the formula (I) is a hydrogen atom or a methoxy group can also be included in the preferable range.

Furthermore, when m is 0 and n is 1 in the formula (I), a compound in which $Z^2$ is —OCO— can also be included in the preferable range.

In addition, when m is 1 and n is 0 in the formula (I), a compound in which $Z^1$ is —COO— can also be included in the preferable range.

Hereinafter, specific examples of the compound represented by the formula (I) will be described, but compounds that can be employed in the invention are not supposed to be restrictively interpreted by the specific examples.

(I-1)

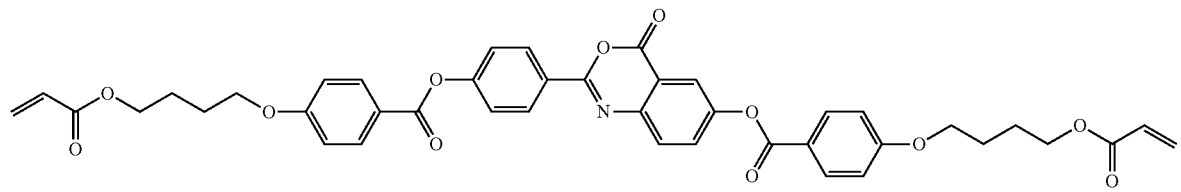

-continued
(I-2)
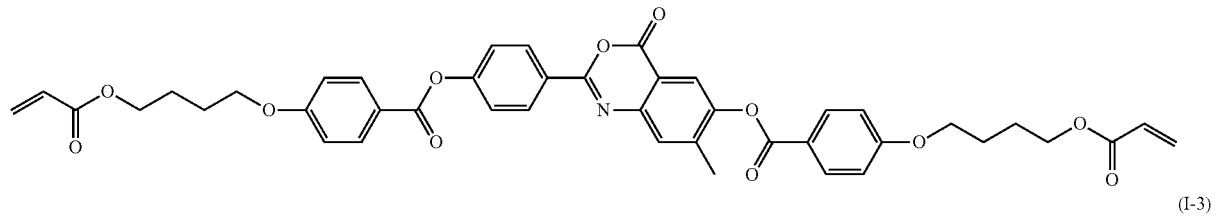
(I-3)
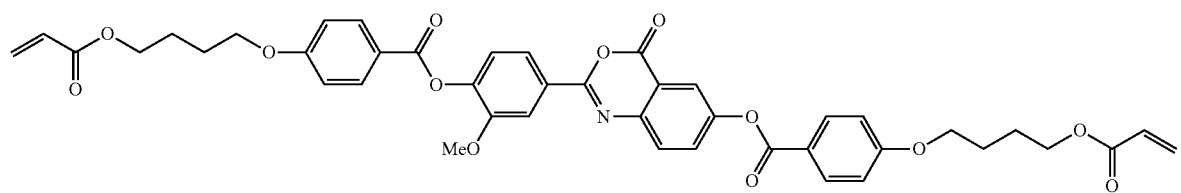
(I-4)
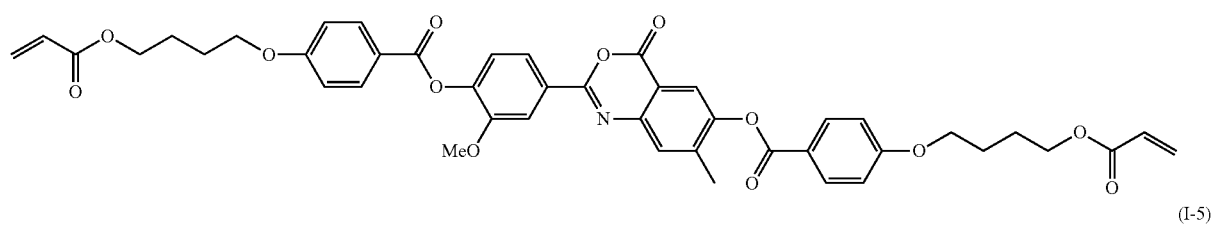
(I-5)
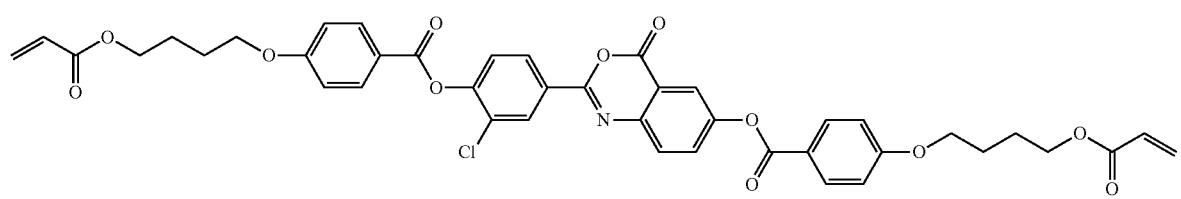
(I-6)
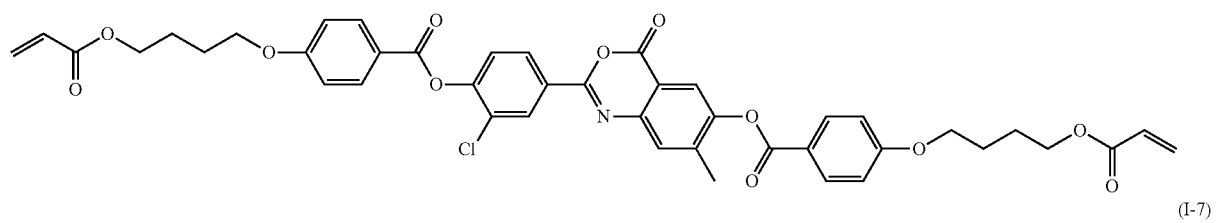
(I-7)
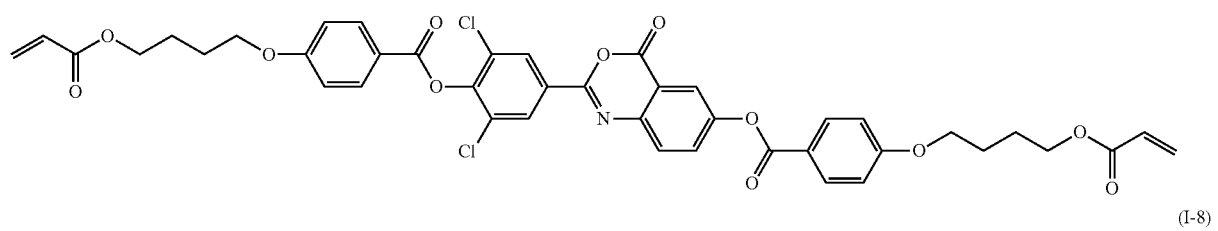
(I-8)
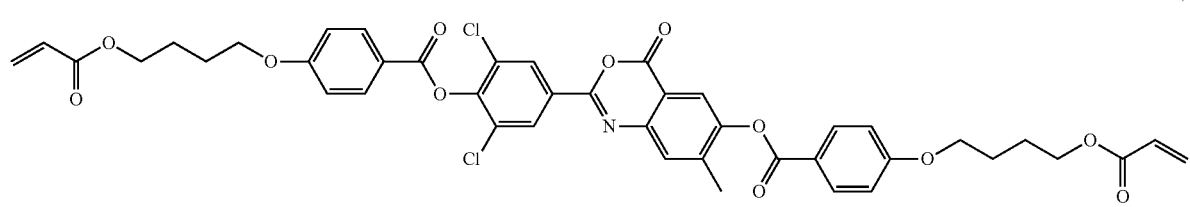

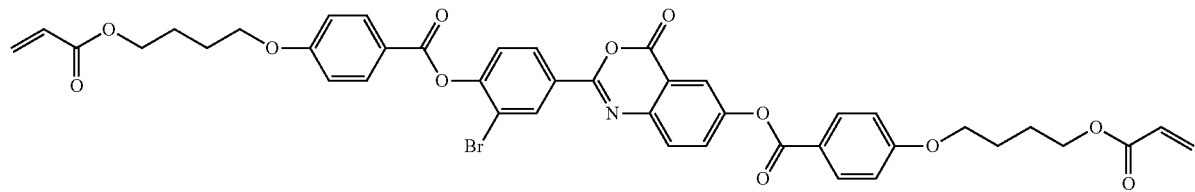
(I-9)
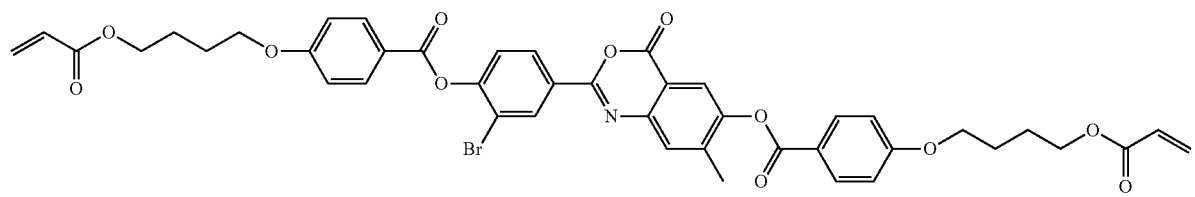
(I-10)
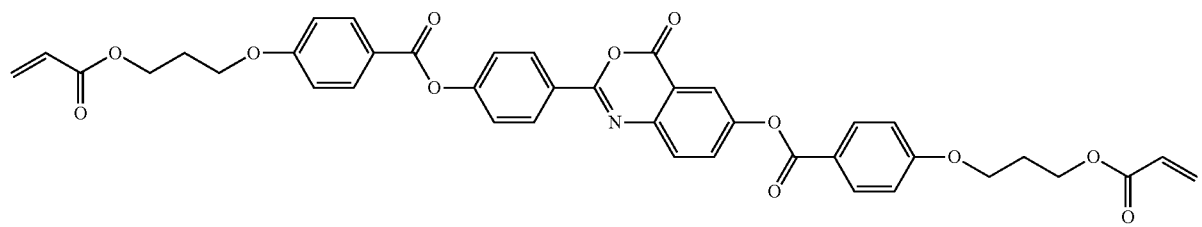
(I-11)
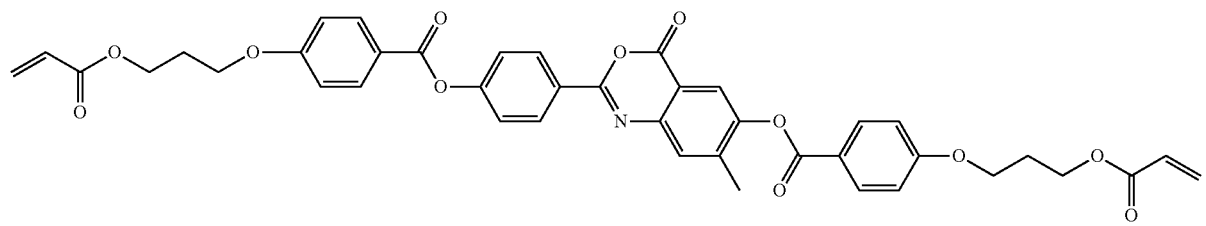
(I-12)
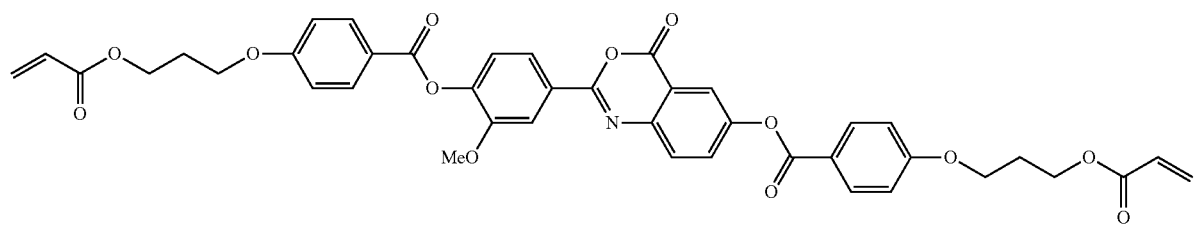
(I-13)
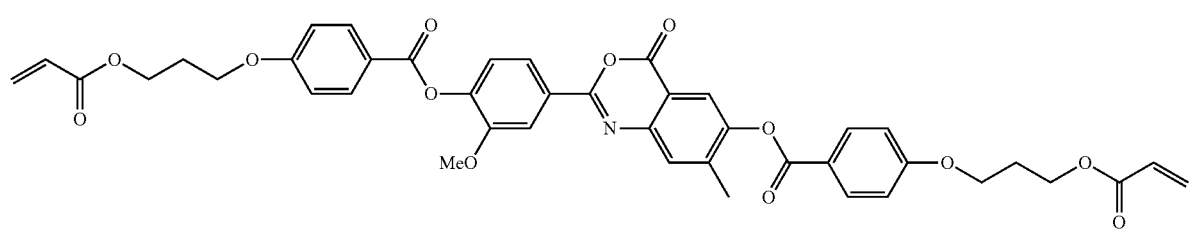
(I-14)

-continued
(I-15)
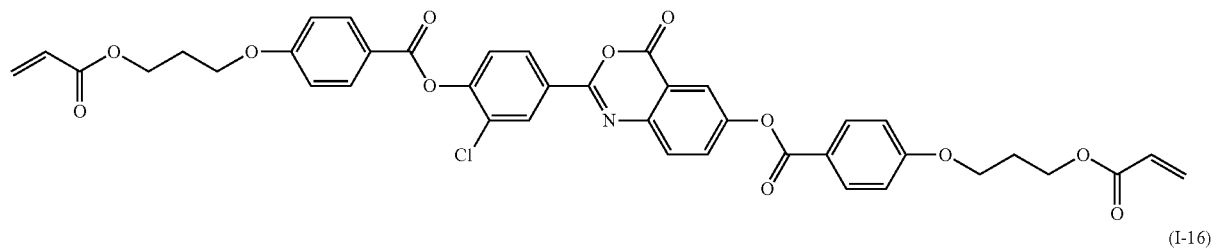
(I-16)
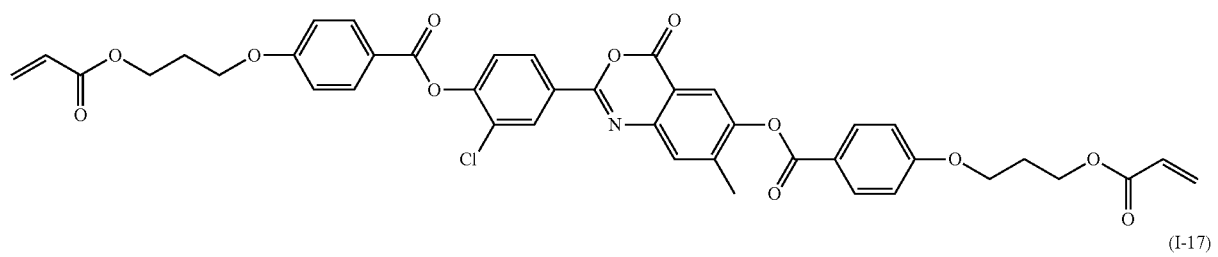
(I-17)
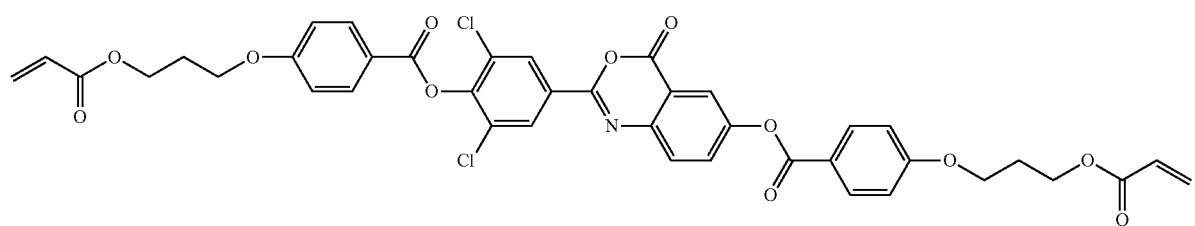
(I-18)
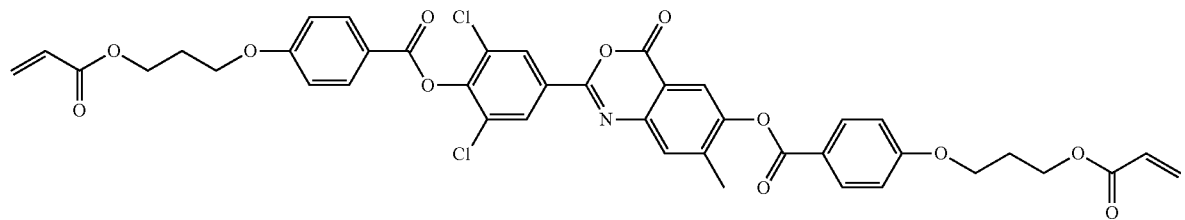
(I-19)
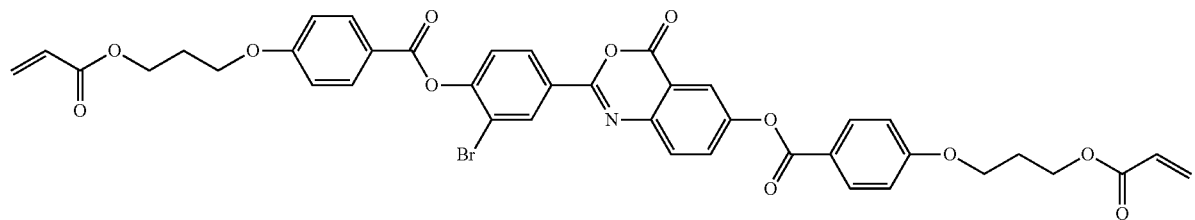
(I-20)
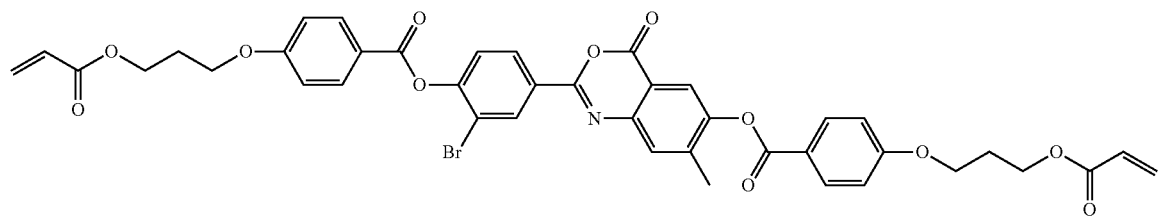

-continued
(I-21)
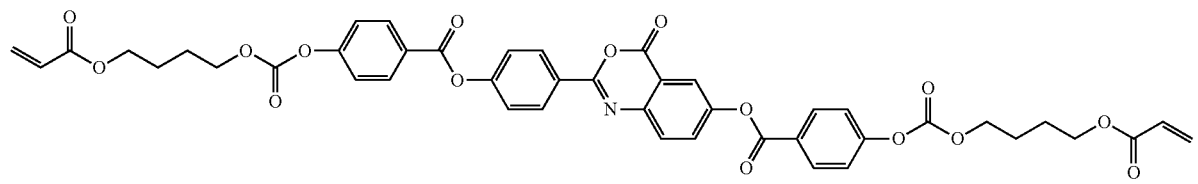
(I-22)
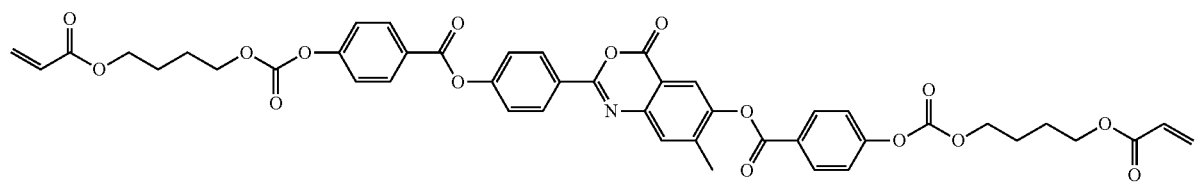
(I-23)
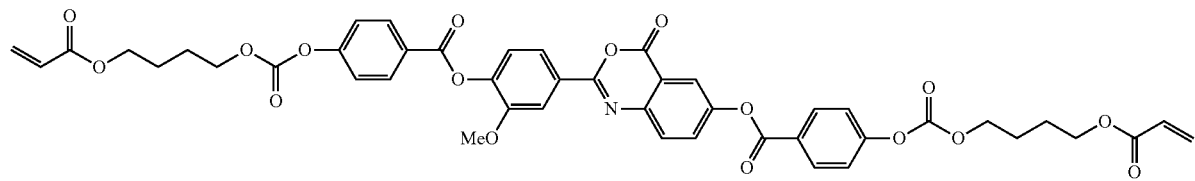
(I-24)
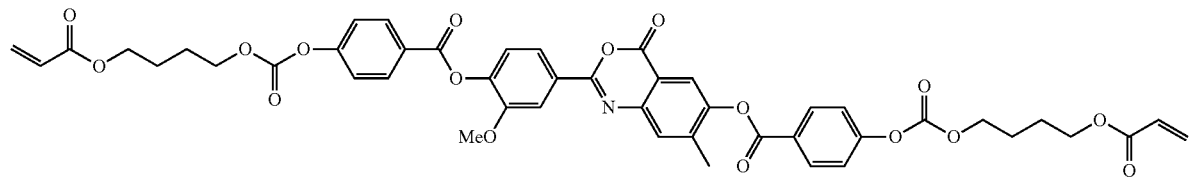
(I-25)
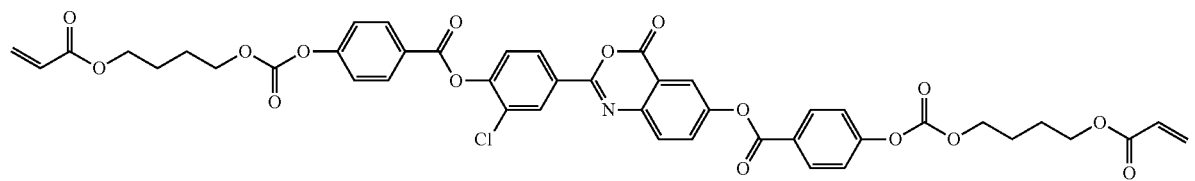
(I-26)
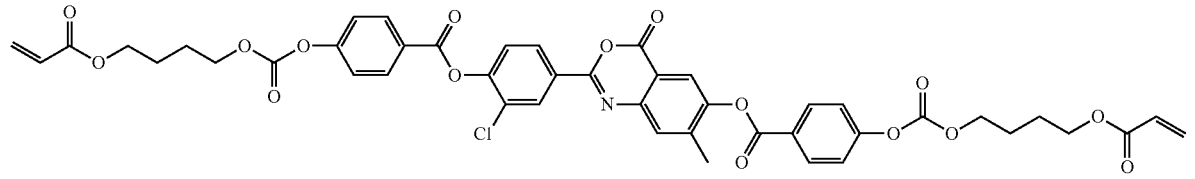
(I-27)
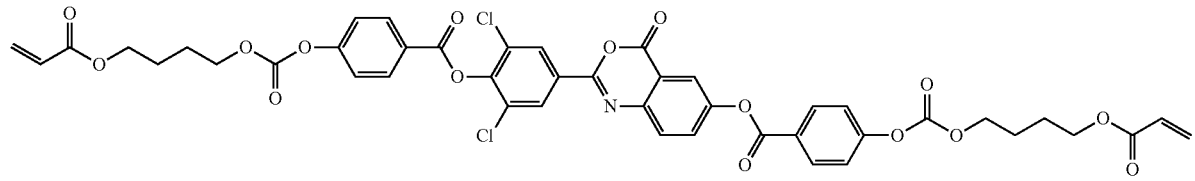

-continued
(I-28)
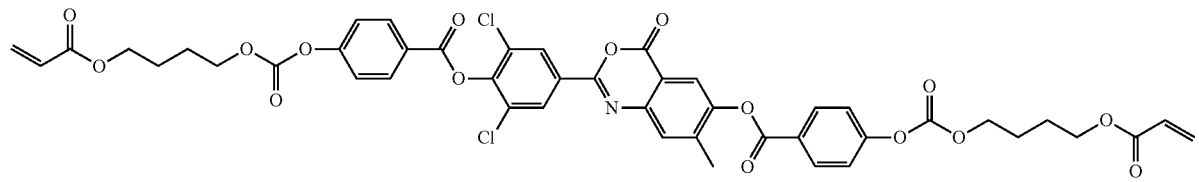
(I-29)
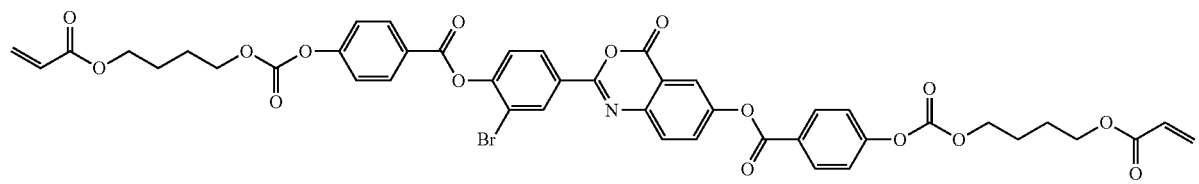
(I-30)
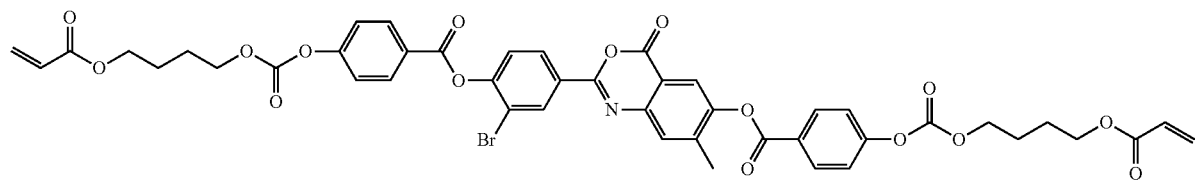
(I-31)
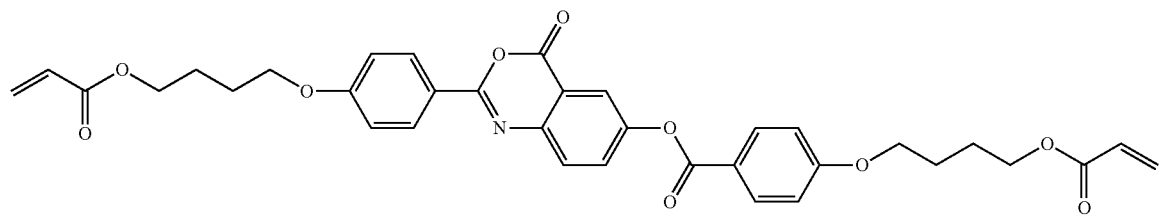
(I-32)
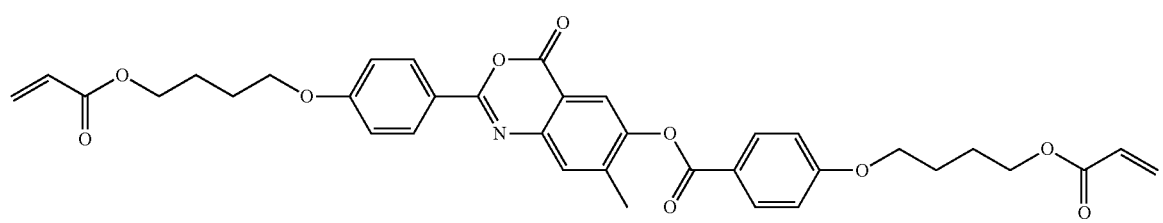
(I-33)
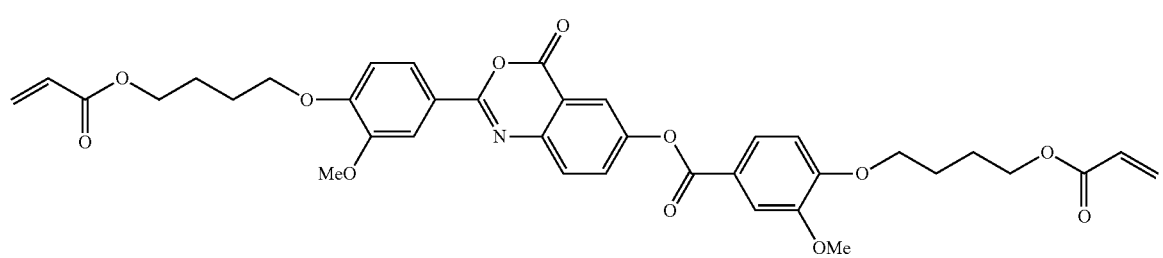

(I-34)
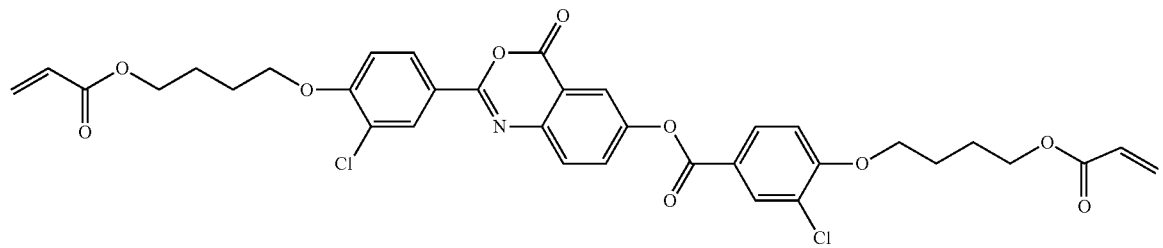
(I-35)
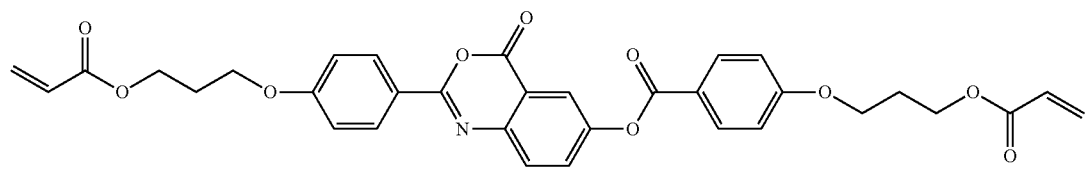
(I-36)
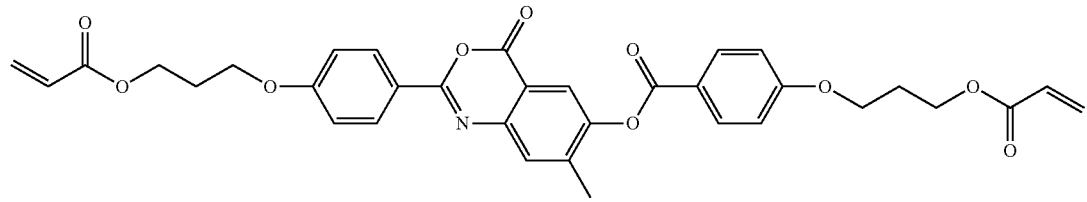
(I-37)
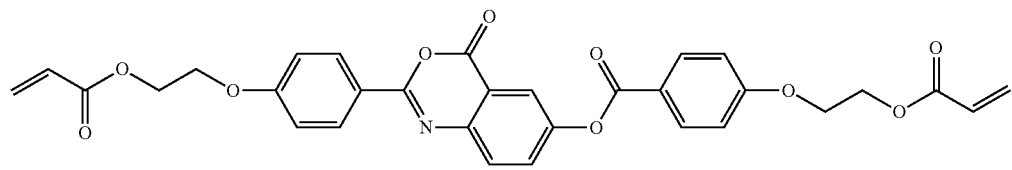
(I-38)
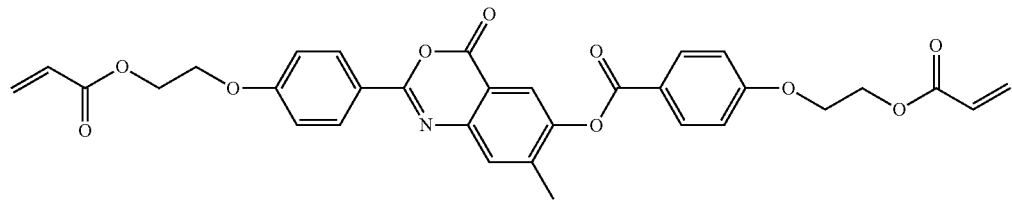
(I-39)
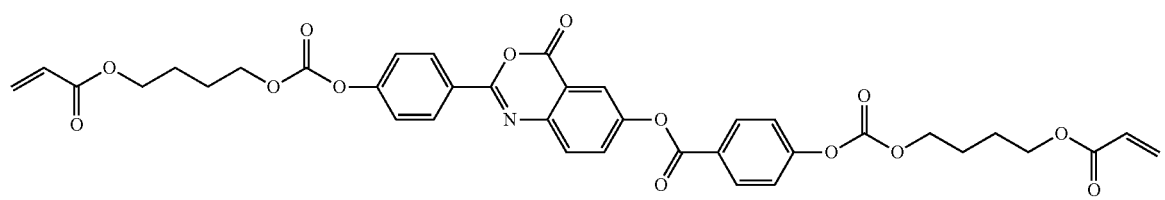
(I-40)
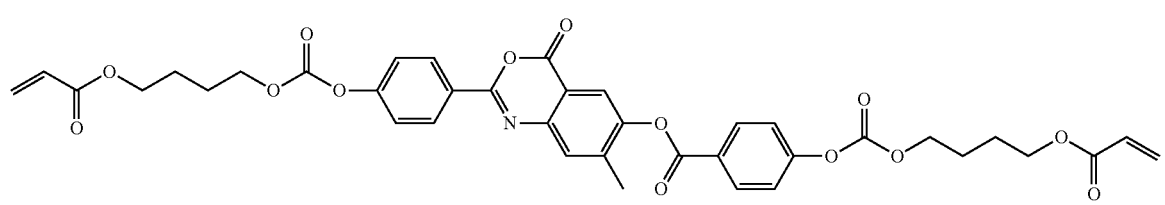

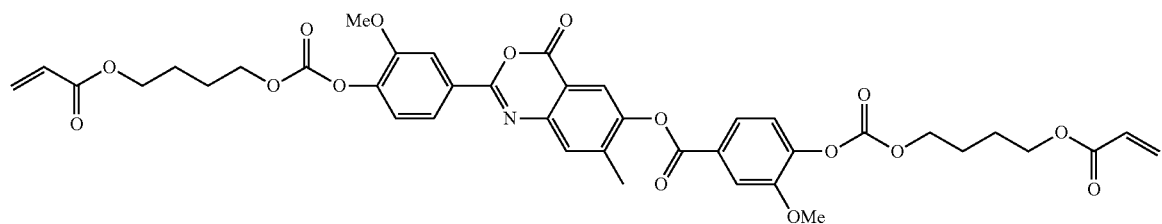
(I-41)
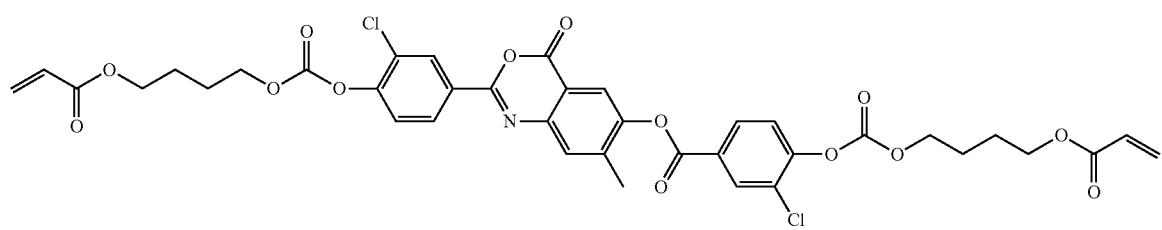
(I-42)
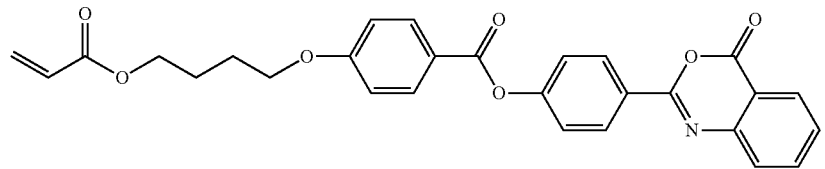
(I-43)
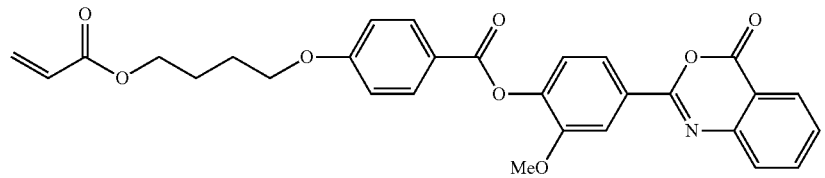
(I-44)
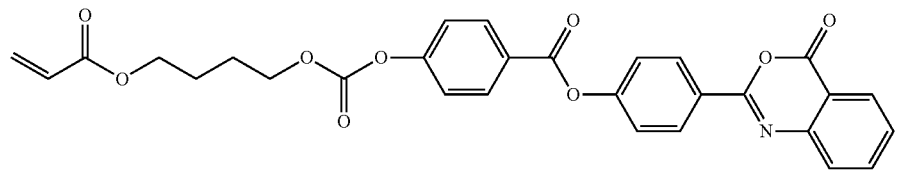
(I-45)
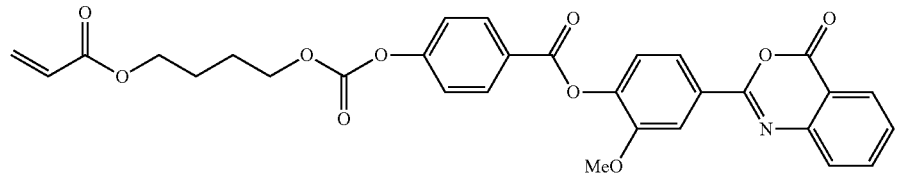
(I-46)
The polymerizable compound of the invention represented by the formula (I) can be manufactured using a variety of methods. For example, the compound can be manufactured using a method in accordance with a reaction formula (1) described below.

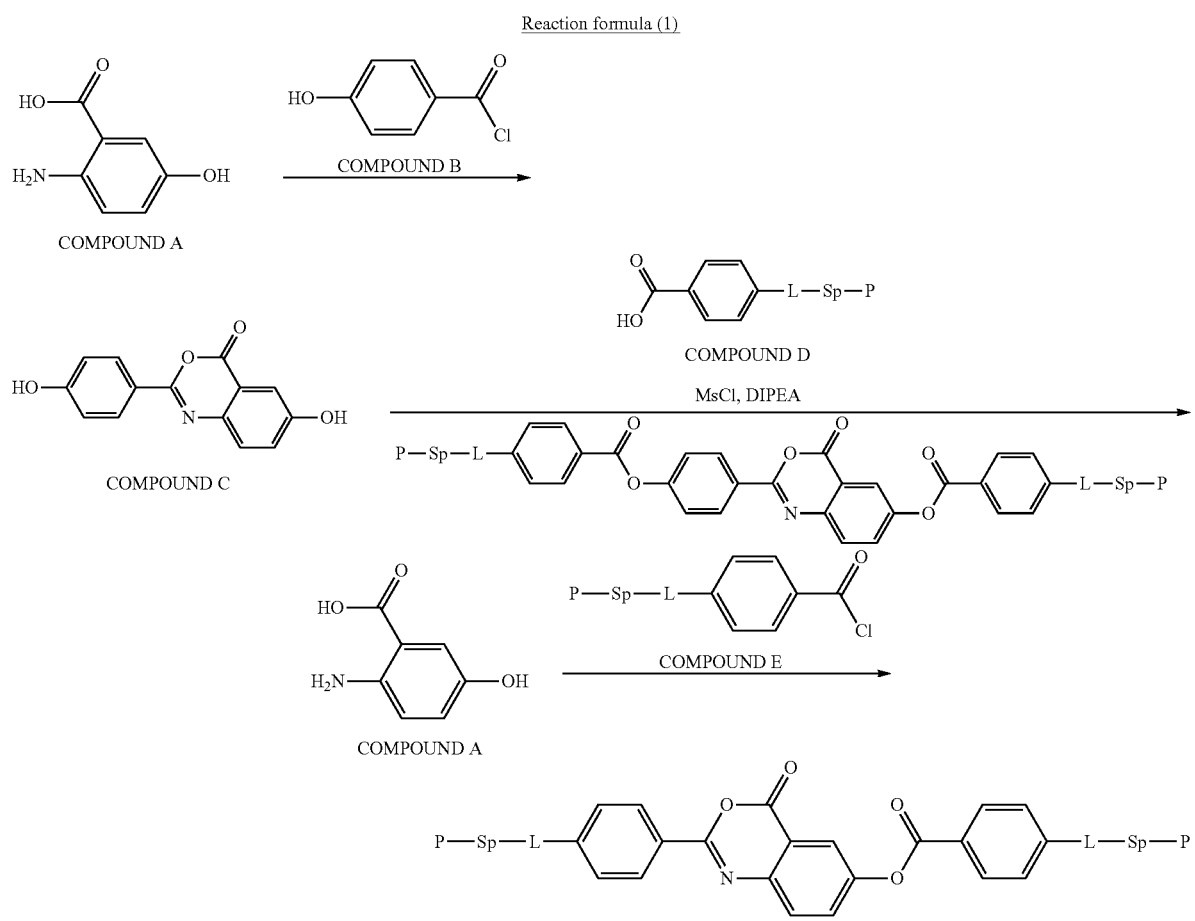

Reaction formula (1)

In the reaction formula (1), the compound A is a hydroxyanthranilic acid derivative, and a commercially available product or a derivative synthesized using a well-known method can be used. In the reaction formula (1), the compound B is a hydroxybenzoic acid derivative, and a commercially available product or a derivative synthesized using a well-known method can be used. Meanwhile, unsubstituted derivatives are illustrated as examples of the compounds A and B, and it is also possible to use a commercially available product or a derivative synthesized using a well-known method which has a substituent at portions represented by $X^1$, $X^2$, $X^3$, $X^4$, $X^5$, $X^6$ and $X^7$ in the reaction formula (1). In addition, the compound D can be synthesized with reference to the method described in [0085] to [0087] on page 10 of JP-A-2002-97170.

That is, the polymerizable compound represented by the formula (I) can be synthesized through, in the reaction formula (1), condensation of the compound A and the compound B, subsequently, synthesis of the compound C through a cyclodehydration reaction, and, subsequently, a reaction between the compound C and the compound D.

Similarly, a tricyclic compound can also be synthesized by condensing the compound E which is derived from the compound D using thionyl chloride or the like with the compound A, and causing a cyclodehydration reaction.

In addition, in order to suppress thermopolymerization during the reaction, a polymerization inhibitor such as a hydroquinone derivative may be used.

Examples of the polymerizable compound of the invention include a liquid crystalline compound. Since the liquid crystalline compound exhibits a high Δn, it can be expected that desired optical characteristics are achieved with a thinner thickness in a film having a fixed orientation compared with a film for which a liquid crystalline compound having a smaller Δn is used.

In addition, the polymerizable compound of the invention satisfies a plurality of characteristics such as being chemically stable, easily dissolved in a solvent, easily polymerized, colorless and transparent. A cured film produced using the compound of the invention can satisfy a plurality of characteristics, such as exhibiting a sufficient hardness, being colorless and transparent, and favorable in terms of weather resistance and thermal resistance. Therefore, a cured film formed using the compound of the invention can be used in a variety of uses, for example, a wave plate, a polarization element, a selective reflection film, a color filter, an antireflection film, a viewing angle compensation film, holography and an oriented film which are components of an optical element.

2. The Polymerizable Composition, Macromolecular Compound and Film of the Invention The invention also provides a polymerizable composition including the compound of the invention (also referred to as the composition of the invention), a macromolecular compound obtained by polymerizing the compound of the invention and a film for which the compound of the invention is used. The polymerizable composition including the compound of the invention preferably contains a chiral agent in addition to the compound of the invention. In addition, the macromolecular compound of the invention is obtained by polymerizing the compound of the invention, and may be liquid crystalline or non-liquid crystalline. The film of the invention is a film obtained using the compound of the invention, and is useful as materials of a variety of optical films such as a wave film and a reflection film. The polymerizable composition, macromolecular compound and film of the invention are particularly preferably a polymerizable composition including the compound represented by the formula (I), a macromolecular compound obtained by polymerizing the compound represented by the formula (I) and a film for which the compound represented by the formula (I) is used. Therefore, in the following description, a case in which the compound of the formula (I) is used will be mainly described as a typical example of the compound of the invention.

An aspect of the composition of the invention is a polymerizable composition containing at least one compound of the formula (I) and at least one chiral compound. A film formed by making the composition of the present aspect into a cholesteric liquid crystalline phase, and then fixing the cholesteric liquid crystalline phase exhibits selective reflection characteristics with respect to light having a predetermined wavelength according to the spiral pitch, and is useful as a reflection film (for example, an infrared ray reflection film). When the polymerizable compound of the invention which exhibits a high Δn is used, there is an advantage that the reflection wavelength band is widened compared with a film having the same thickness for which a liquid crystalline compound having a lower Δn is used.

In the composition of the invention, the compound of the formula (I) may be a principal component or may be used as an additive. When 5 mass % or more of the compound of the formula (I) is included with respect to the total mass of the composition, the effect of the compound of the formula (I) can be obtained, and the content of the compound is preferably 10 mass % to 85 mass %, more preferably 10 mass % to 75 mass %, and still more preferably 15 mass % to 70 mass %. However, the content is not limited to the above ranges.

(1) Chiral Compound

In order to prepare the composition of the invention as a composition exhibiting a cholesteric liquid crystalline phase, a chiral compound is preferably added. The chiral compound may be liquid crystalline or non-liquid crystalline. The chiral compound can be selected from a variety of well-known chiral agents (described in, for example, Paragraph 4-3, Chapter 3, Liquid Crystalline Device Handbook; pp. 199, Chiral Agents for TN and STN; Japan Society for the Promotion of Science—142 (C) committee (1989)). The chiral compound generally includes an asymmetric carbon atom, but an axial asymmetric compound or a planar asymmetric compound including no asymmetric carbon atom can be also used. Examples of the axial asymmetric compound or the planar asymmetric compound include binaphthyls, helicene, paracyclophane and derivatives thereof. The chiral compound (chiral agent) may include a polymerizable group. In a case in which the chiral compound includes a polymerizable group and a jointly used rod-shaped liquid crystalline compound also includes a polymerizable group, it is possible to form a polymer having a repeating unit derived from the rod-shaped liquid crystalline compound and a repeating unit derived from the chiral compound using a polymerization reaction between the polymerizable chiral compound and the polymerizable rod-shaped liquid crystalline compound. In this aspect, the polymerizable group included in the polymerizable chiral compound is preferably the same group as the polymerizable group included in the polymerizable rod-shaped liquid crystalline compound. Therefore, the polymerizable group of the chiral compound is also preferably an unsaturated polymerizable group, an epoxy group or an aziridinyl group, more preferably an unsaturated polymerizable group, and particularly preferably an ethylenic unsaturated polymerizable group.

There is preferably 1 mol % to 30 mol % of the chiral compound in the composition of the invention with respect to the compound of the formula (I) being jointly used. The use amount of the chiral compound is preferably smaller since there are more cases in which the liquid crystallinity is not influenced. Therefore, the chiral compound is preferably a compound having a strong torsion so that a desired torsional orientation of the spiral pitch can also be achieved in a small amount. Examples of the above chiral agent that exhibits a strong torsion include the chiral agent described in JP-A-2003-287623, which can be preferably used in the invention.

(2) Other Liquid Crystalline Compounds

The composition of the invention may contain one or more other liquid crystalline compounds together with the compound of the formula (I). Since the compound of the formula (I) also has a high compatibility with other liquid crystalline compounds, even when other liquid crystalline compounds are mixed in, it is possible to form a highly transparent film without causing the film to be oblique or the like. Since other liquid crystalline compounds can be jointly used, it is possible to provide compositions having a variety of compositions which are suitable for a variety of uses. An example of other liquid crystalline compounds that can be jointly used is a rod-shaped nematic liquid crystalline compound. Examples of the rod-shaped nematic liquid crystalline compound include azomethines, azoxys, cyanobiphenyls, cyanophenyl esters, bezoic acid esters, cyclohexane carboxylic acid phenyl esters, cyanophenyl cyclohexanes, cyano-substituted phenylpyrimidines, alkoxy-substituted phenylpyrimidines, phenyl dioxanes, tolans and alkenyl cyclohexyl benzonitriles. It is possible to use not only a low-molecular-weight liquid crystalline compound but also a macromolecular liquid crystalline compound.

The other liquid crystalline compounds that can be used in the invention may be polymerizable or non-polymerizable. A variety of documents (for example, Y. Goto et. al., Mol. Cryst. Liq. Cryst. 1995, Vol. 260, pp. 23-28) describe a rod-shaped liquid crystalline compound having no polymerizable group.

The polymerizable rod-shaped liquid crystalline compound can be obtained by introducing a polymerizable group into the rod-shaped liquid crystalline compound. Examples of the polymerizable group include unsaturated polymerizable groups, epoxy groups and aziridinyl groups, and the polymerizable group is preferably an unsaturated polymerizable group and particularly preferably an ethylenic unsaturated polymerizable group. The polymerizable group can be introduced into the molecules of the rod-shaped liquid crystalline compound using a variety of methods. The number of the polymerizable groups included in the polymerizable rod-shaped liquid crystalline compound is preferably 1 to 6 and more preferably 1 to 3. Examples of the polymerizable rod-shaped liquid crystalline compound include compounds described in Makromol. Chem., Vol. 190. pp. 2255 (1989), Advanced Materials Vol. 5, pp. 107 (1993), the specification of U.S. Pat. No. 4,683,327, the specification of U.S. Pat. No. 5,622,648, the specification of U.S. Pat. No. 5,770,107, International Publication No. WO95/22586, International Publication No. WO95/24455, International Publication No. WO97/00600, International Publication No. WO98/23580, International Publication No. WO98/52905, JP-A-1-272551, JP-A-6-16616, JP-A-7-110469, JP-A-11-80081, JP-A-2001-328973 and the like. Two or more polymerizable rod-shaped liquid crystalline compounds may be jointly used. When two or more polymerizable rod-shaped liquid crystalline compounds are jointly used, it is possible to decrease the orientation temperature.

The addition amount of the other liquid crystalline compound is not particularly limited. The content fraction of the compound of the formula (I) may be high, the content fraction of the other liquid crystalline compound may be high, the content fractions of the compound of the formula (I) and the other liquid crystalline compound may be the same, and can be adjusted in a preferable range depending on use.

(3) Polymerization Initiator

The composition of the invention preferably contains a polymerization initiator. For example, in an aspect in which a curing reaction is made to proceed by radiating ultraviolet rays so as to form a cured film, a polymerization initiator being used is preferably a photopolymerization initiator that can initiate a polymerization reaction using the radiation of ultraviolet rays. Examples of the photopolymerization initiator include α-carbonyl compounds (described in the specifications of U.S. Pat. No. 2,367,661 and U.S. Pat. No. 2,367,670), acyloin ether (described in the specification of U.S. Pat. No. 2,448,828), α-hydrocarbon-substituted aromatic acyloin compounds (described in the specification of U.S. Pat. No. 2,722,512), polynuclear quinone compounds (described in the specifications of U.S. Pat. No. 3,046,127 and U.S. Pat. No. 2,951,758), a combination of triarylimidazole dimer and p-aminophenyl ketone (described in the specification of U.S. Pat. No. 3,549,367), acridine and phenazine compounds (described in the specifications of JP-A-60-105667 and U.S. Pat. No. 4,239,850), oxadiazole compounds (described in the specification of U.S. Pat. No. 4,212,970) and the like.

The use amount of the photopolymerization initiator is preferably 0.1 mass % to 20 mass % of the composition (solid content in the case of a coating fluid), and more preferably 1 mass % to 8 mass %.

(4) Orientation Controlling Agent

An orientation controlling agent that contributes to the stable and fast formation of a liquid crystalline phase (for example, a cholesteric liquid crystalline phase) may be added to the composition of the invention. Examples of the orientation controlling agent include fluorine-containing (meth) acrylate-based polymers and compounds represented by the following formulae (X1) to (X3). The composition of the invention may contain two or more selected from the above. The above compounds can reduce or substantially horizontally orient the tilt angle of the molecules of the liquid crystalline compound in the air interface of the layer. Further, in the specification, "horizontal orientation" refers to the long axes of liquid crystalline molecules and the film surface being parallel, but the horizontal orientation does not require the long axes of liquid crystalline molecules and the film surface to be strictly parallel, and, in the specification, means an orientation in which the inclination angle from the horizontal surface is less than 20 degrees. In a case in which the liquid crystalline compound is horizontally oriented in the vicinity of the interface with the air, orientation defects are not easily caused, and therefore the transparency in the visible light range is enhanced. On the other hand, when the molecules of the liquid crystalline compound are oriented at a large tilt angle, for example, in a case in which a cholesteric liquid crystalline phase is formed, since the spiral axis deviates from the film surface normal line, the reflectivity decreases or a finger print pattern is caused, and haze increases or diffraction properties appear, which are not preferable.

Examples of the fluorine-containing (meth) acrylate-based polymers that can be used as the orientation controlling agent are described in [0018] to [0043] and the like in JP-A-2007-272185.

Hereinafter, the following formulae (X1) to (X3) that can be used as the orientation controlling agent will be sequentially described.

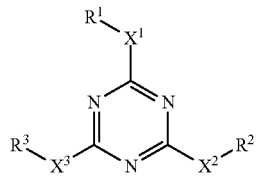

Formula (X1)

In the formula, each of $R^1$, $R^2$ and $R^3$ independently represents a hydrogen atom or a substituent, and $X^1$, $X^2$ and $X^3$ represent a single bond or divalent linking group. The substituents respectively represented by $R^1$ to $R^3$ are preferably substituted or unsubstituted alkyl groups (among the alkyl groups, an unsubstituted alkyl group or a fluorine-substituted alkyl group is more preferable), aryl groups (among the aryl groups, an aryl group having a fluorine-substituted alkyl group is preferable), substituted or unsubstituted amino groups, alkoxy groups, alkylthio groups, or a halogen atom. The divalent linking groups respectively represented by $X^1$, $X^2$ and $X^3$ are preferably alkylene groups, alkenylene groups, divalent aromatic groups, divalent hetero ring residues or divalent linking groups selected from a group consisting of —CO—, —NRa- (Ra is an alkyl group having 1 to 5 carbon atoms or a hydrogen atom), —O—, —S—, —SO—, —SO$_2$— and combinations thereof. The divalent linking group is more preferably an alkylene group, a phenylene group, a divalent linking group selected from a group consisting of —CO—, —NRa-, —O—, —S—, and —SO$_2$— or a divalent linking group that is a combination of at least two groups selected from the above group. The number of carbon atoms in the alkylene group is preferably 1 to 12. The number of carbon atoms in the alkenylene group is preferably 2 to 12. The number of carbon atoms in the divalent aromatic group is preferably 6 to 10.

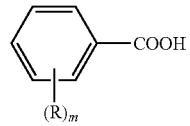

Formula (X2)

In the formula, R represents a substituent, and m represents an integer of 0 to 5. In a case in which m represents an integer of 2 or more, a plurality of Rs may be equal or different. A preferable substituent as R is the same as the substituents included in the preferable range of the substituent represented by $R^1$, $R^2$ and $R^3$. m preferably represents an integer of 1 to 3, and particularly preferably represents 2 or 3.

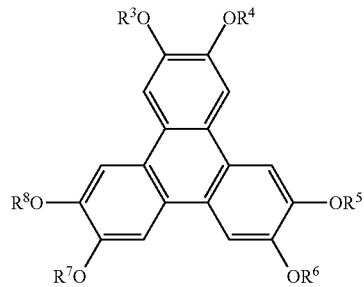

Formula (X3)

In the formula, each of $R^4$, $R^5$, $R^6$, $R^7$, $R^8$ and $R^9$ independently represents a hydrogen atom or a substituent. The substituents respectively represented by $R^4$, $R^5$, $R^6$, $R^7$, $R^8$ and $R^9$ are preferably the same as the substituents exemplified as the preferable substituents represented by $R^1$, $R^2$ and $R^3$ in the formula (XI).

Examples of the compound represented by the formula (X1) to (X3) which can be used as the orientation controlling agent in the invention include compounds described in JP-A-2005-99248.

Meanwhile, in the invention, as the orientation controlling agent, one of the compounds represented by the formulae (X1) to (X3) may be solely used, or two or more compounds may be jointly used.

The amount of the compound represented by any one of the formulae (X1) to (X3) added to the composition is preferably 0.01 mass % to 10 mass %, more preferably 0.01 mass % to 5 mass %, and particularly preferably 0.02 mass % to 1 mass % of the mass of the compound of the formula (I).

(5) Other Additives

The composition of the invention may contain one or two or more other additives such as an antioxidant, an ultraviolet absorbent, a sensitizer, a stabilizer, a plasticizer, a chain transfer agent, a polymerization inhibitor, a defoamer, a leveling agent, a thickener, a flame retardant, a surfactant, a dispersant and a coloring material such as a dye and a pigment.

(6) Method for Producing a Film Using the Composition

The composition of the invention is useful as a material of a variety of optical films, such as a phase difference film and a reflection film. An example of the method for manufacturing the film is a manufacturing method including at least (i) the polymerizable composition of the invention is coated on the surface of a substrate or the like, and made into a state of a liquid crystalline phase (cholesteric liquid crystalline phase or the like), and (ii) a curing reaction of the polymerizable composition is made to proceed so as to fix the liquid crystalline phase and form a cured film.

It is also possible to produce a film in which a plurality of the cured films are laminated by repeating the (i) and (ii) steps a plurality of times.

In the (i) step, first, the polymerizable composition of the invention is coated on the surface of the substrate or an orientation film formed on the substrate. The composition is preferably prepared as a coating fluid in which a material is dissolved and/or dispersed in a solvent. As the solvent used to prepare the coating fluid, an organic solvent is preferably used. Examples of the organic solvent include amides (for example, N,N-dimethylformamide); sulfoxides (for example, dimethyl sulfoxide); hetero ring compounds (for example, pyridine); hydrocarbons (for example, benzene and hexane); alkyl halides (for example, chloroform and dichloromethane); esters (for example, methyl acetate and butyl acetate); ketones (for example, acetone, methyl ethyl ketone); ethers (for example, tetrahydrofuran and 1,2-dimethoxyethane); 1,4-butanediol diacetate; and the like. Among the above, alkyl halides and ketones are particularly preferable. Two or more organic solvents may be jointly used.

The coating fluid can be coated using a variety of methods, such as a wire bar coating method, an extrusion coating method, a direct gravure coating method, a reverse gravure coating method and a die coating method. In addition, it is also possible to form a coated film by ejecting the composition from a nozzle using an ink jet apparatus.

Next, the composition which has been coated on the surface and become the coated film is made into a state of a liquid crystalline phase such as a cholesteric liquid crystalline phase. In an aspect in which the composition is prepared as a coating fluid including a solvent, there is a case in which the composition is made into a state of a liquid crystalline phase by drying the coated film and removing the solvent. In addition, in order to achieve a transition temperature to the liquid crystalline phase, the coated film may be heated as desired. For example, when the coated film is temporarily heated to a temperature of an isotropic phase, and then cooled to a liquid crystalline phase transition temperature, it is possible to stably make the composition into a state of a liquid crystalline phase. The liquid crystalline phase transition temperature of the composition is preferably in a range of 10° C. to 250° C., and more preferably in a range of 10° C. to 150° C. in terms of manufacturing ability and the like. When the liquid crystalline phase transition temperature is lower than 10° C., there is a case in which a cooling step or the like becomes necessary in order to decrease the temperature to a temperature range in which a liquid crystalline phase is exhibited. In addition, when the liquid crystalline phase transition temperature exceeds 200° C., a high temperature is required in order to make the composition into an isotropic liquid state at a higher temperature than the temperature range in which a liquid crystalline phase is temporarily exhibited, and it becomes disadvantageous in terms of the consumption of heat energy, the deformation and modification of the substrate, and the like.

Next, in the (ii) step, the coated film that has been made into the state of a liquid crystalline phase is cured. The coated film may be cured according to any polymerization method such as a radical polymerization method, an anionic polymerization method, a cationic polymerization method or a coordination polymerization method. A suitable polymerization method is selected depending on the compound of the formula (I). A polymer having a unit derived from the compound of the formula (I) of the invention in a constituent unit can be obtained from the polymerization.

In an example, the curing reaction is made to proceed by radiating ultraviolet rays. For the radiation of ultraviolet rays, a light source such as an ultraviolet ray lamp is used. In this step, the curing reaction of the composition is made to proceed by radiating ultraviolet rays, and the cholesteric liquid crystalline phase is fixed, thereby forming a cured film.

The radiation energy amount of the ultraviolet rays is not particularly limited, and, in general, preferably approximately 100 mJ/cm$^2$ to 800 mJ/cm$^2$. In addition, the radiation time of ultraviolet rays on the coated film is not particularly limited, but determined from the viewpoint of both the sufficient strength and productivity of the cured film.

In order to promote the curing reaction, ultraviolet rays may be radiated under heating conditions. In addition, the temperature during the radiation of ultraviolet rays is preferably maintained in a temperature range in which the liquid crystalline phase is exhibited so as to prevent the liquid crystalline phase from being disarrayed. In addition, since the oxygen concentration of the atmosphere has a relationship with the degree of polymerization, in a case in which a desired degree of polymerization is not achieved in the air and the film strength is not sufficient, the oxygen concentration in the atmosphere is preferably decreased using a method of nitrogen purging or the like.

In the above step, the liquid crystalline phase is fixed, thereby forming a cured film. Here, the most typical and preferable aspect of the state of the liquid crystalline phase "being solidified" is a state in which the orientation of the compound that forms the liquid crystalline phase is held. In addition to the above state, specifically, the state of the liquid crystalline phase "being solidified" refers to a state in which the layer is not fluidic, generally, at 0° C. to 50° C. or in a temperature range of −30° C. to 70° C. under more severe conditions, and the fixed orientation pattern can be continuously held stably without causing a change in the orientation pattern due to an external field or an external force. In the invention, the orientation state of the liquid crystalline phase is fixed using the curing reaction progressed by the radiation of ultraviolet rays.

Meanwhile, in the invention, it is simply required for the optical properties of the liquid crystalline phase to be held in the layer, and, ultimately, the composition in the cured film does not need to exhibit liquid crystallinity. For example, the composition may lose liquid crystallinity due to an increase in the molecular weight from the curing reaction.

The thickness of the cured film is not particularly limited. A preferable film thickness is determined depending on use or desired optical characteristics. In general, the thickness is preferably 0.05 µm to 50 µm, and more preferably 1 µm to 35 µm.

(7) Substrate

The film of the invention may have a substrate. The substrate is self-supportive, and there is no limitation in the materials and optical characteristics as long as the substrate supports the cured film. The substrate can be selected from a glass plate, a quartz plate, a polymer film and the like. Depending on use, a high transparency with respect to ultraviolet light is required. Examples of polymer films that are highly transparent with respect to visible light include a variety of polymer films for optical films which are used as a member of a display apparatus, such as a liquid crystal display apparatus. Examples of the substrate include polyester films such as polyethylene terephthalate (PET), polybutylene terephthalate and polyethylene naphthalate (PEN); polycarbonate (PC) films, polymethyl methacrylate films; polyolefin films such as polyethylene and polypropylene; polyimide films, triacetyl cellulose (TAC) films and the like. Polyethylene terephthalate and triacetyl cellulose are preferable.

(8) Orientation Layer

The film of the invention may also include an orientation layer between the substrate and the cured film. The orientation layer has a function of more precisely regulating the orientation direction of the liquid crystalline compound. The orientation layer can be provided using means such as a rubbing treatment of an organic compound (preferably a polymer), oblique evaporation of an inorganic compound, formation of a layer having a microgroove or the like. Furthermore, orientation layers in which an orientation function is generated by supply of an electric field, supply of a magnetic field or radiation of light is also known. The orientation layer is preferably formed on the surface of a polymer film through a rubbing treatment.

The material used for the orientation layer is preferably a polymer of an organic compound, and a crosslinkable polymer or a polymer that is crosslinked using a crosslinking agent is frequently used. Needless to say, a polymer having both functions also can be used. Examples of the polymer include polymers, such as polymethyl methacrylate, acrylic acid/methacrylic acid copolymers, styrene/malein imide copolymers, polyvinyl alcohols and denatured polyvinyl alcohols, poly(N-methylol acrylamide), styrene/vinyl toluene copolymers, polyethylene chlorosulfonate, nitrocellulose, polyvinyl chloride, chlorinated polyolefin, polyesters, polyimides, vinyl acetate/vinyl chloride copolymers, ethylene/vinyl acetate copolymers, carboxymethyl cellulose, gelatin, polyethylene, polypropylene and polycarbonate, and compounds, such as a silane coupling agent. An example of the preferable polymer is an aqueous polymer, such as poly (N-methylol acrylamide), carboxymethyl cellulose, gelatin, polyvinyl alcohols or denatured polyvinyl alcohol, gelatin, polyvinyl alcohol and denatured polyvinyl alcohol are more preferable, and polyvinyl alcohol and denatured polyvinyl alcohol are particularly preferable.

(9) Use of the Film of the Invention

An aspect of the film of the invention is a film in which the orientation (for example, horizontal orientation, vertical orientation, hybrid orientation and the like) of the liquid crystalline phase in the polymerizable composition of the invention is fixed, and is a film that exhibits optical anisotropy. The film is used as an optical compensation film or the like in a liquid crystal display apparatus and the like.

An aspect of the film of the invention is a film in which the cholesteric liquid crystalline phase of the polymerizable composition of the invention is fixed, and is a film that exhibits selective reflection characteristics with respect to light in a predetermined wavelength range. The film that exhibits selective reflection characteristics in an infrared ray wavelength range (wavelength 800 nm to 1300 nm) is adhered to window glass of, for example, buildings or vehicles or combined with laminated glass, and used as a heat shielding member.

In addition, the film of the invention can be used in a variety of uses, for example, a polarization element, a selective reflection film, a color filter, an antireflection film, a viewing angle compensation film, holography and an oriented film which are components of an optical element.

EXAMPLES

Hereinafter, the characteristics of the invention will be more specifically described using examples and comparative examples (meanwhile, the comparative examples are not always well-known related art). Materials, use amounts, fractions, treatment contents, treatment order and the like described in the following examples can be appropriately changed within the scope of the purport of the invention. Therefore, the range of the invention is not supposed to be restrictively interpreted based on specific examples described below.

1. The Synthesis and Physical Properties of the Compounds of the Formula (I)

Example 1

Synthesis of Compound (I-1A)

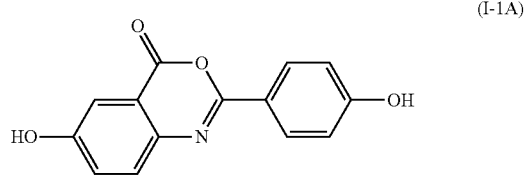 [SMILES: O=c1oc(-c2ccc(O)cc2)nc2ccc(O)cc12]

Thionyl chloride (7.9 ml, 108.6 mmol) was added dropwise to a solution obtained by dissolving 4-hydroxybenzoic acid (10.0 g, 72.4 mmol) in tetrahydrofuran (30 ml) and N,N-dimethyl formamide (500 µl), and the resulting solution was stirred as it was at room temperature for 1 hour. A solution obtained by dissolving 4-hydroxyanthranilic acid (5.54 g, 36.2 mmol) in N-ethyl pyrrolidone (30 ml) was added to the solution obtained above, pyridine (6 ml) was carefully added at room temperature, and the resulting solution was stirred at room temperature for 2 hours. An aqueous solution of 0.5 mol/L hydrochloric acid (150 ml) was added to the obtained reaction fluid, generated white solids were filtered off, and the solution was washed using water (50 ml) twice, thereby obtaining Compound (I-1A) (5.7 g, percentage yield 62%) as a white solid.

1H-NMR (d6-DMSO): δ=6.93 (m, 2H), 7.35 (dd, 1H), 7.40 (d, 1H), 7.55 (d, 1H), 8.00 (m, 2H), δ=10.4 (brs, 2H)

Synthesis of Compound (I-1)

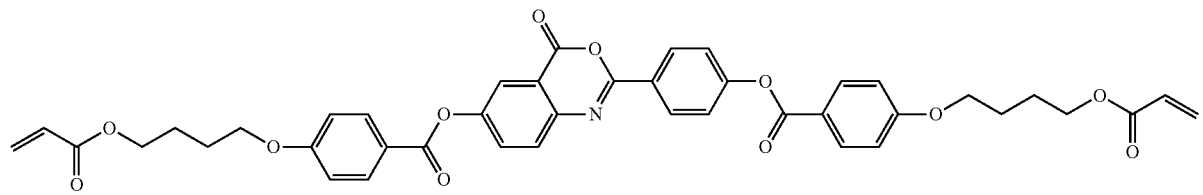

(I-1)

MsCl (1.9 ml, 24.5 mmol) and THF (10 ml) were added to a three-necked flask, the flask was immersed in an ice and methanol bath, and the temperature in the flask was set to −5° C. While maintaining the temperature in the flask at 5° C. or lower, a liquid mixture of 4-acryloyloxybenzoic acid (6.42 g, 24.3 mmol)/diisopropylethylamine (hereinafter referred to as DIPEA) (4.32 ml, 24.8 mmol)/2,6-di-t-butyl-4-methylphenol (0.10 g)/THF (20 ml) was added dropwise to the above solution. The solution was held at 5° C. or lower, stirred for 2 hours, and then DIPEA (4.32 ml, 24.8 mmol) and N,N-dimethyl-4-aminopyridine (hereinafter referred to as DMAP, 0.1 g) were added. A solution obtained by dissolving the compound (I-1A) (3.0 g, 11.7 mmol) in N-ethyl pyrrolidone (15 ml) was added dropwise to the obtained solution, and the resulting solution was stirred at room temperature for 3 hours. An aqueous solution of 0.5 mol/L hydrochloric acid (100 ml) was added to a reaction fluid, and generated white solids were filtered off. The obtained white solid was recrystallized using dichloromethane/methanol, thereby obtaining Compound (I-1) (7.10 g, percentage yield 81%) which is a white solid.

1H-NMR (CDCl$_3$): δ=1.8-2.0 (m, 8H), 4.0-4.2 (m, 4H), 4.2-4.3 (m, 4H), 5.83 (d, 2H), 6.12 (dd, 2H), 6.42 (d, 2H), 6.90-7.05 (m, 4H), 7.39 (d, 2H), 7.68 (dd, 1H), 7.72 (d, 1H), 8.07 (d, 1H), 8.1-8.2 (m, 4H), 8.38 (m, 2H)

Example 2

Synthesis of Compound (I-3A)

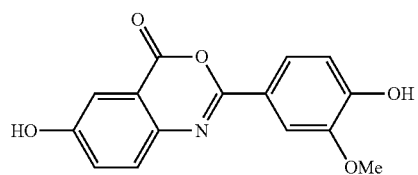

(I-3A)

The compound was synthesized using the same method as in Example 1 except that vanillic acid was used instead of 4-hydroxybenzoic acid. The yield was 4.2 g (percentage yield 41%).

1H-NMR (d6-DMSO): δ=3.86 (s, 3H), 6.94 (d, 1H), 7.34 (dd, 1H), 7.40 (d, 1H), 7.55 (d, 1H), 7.64 (m, 2H), δ=10.0 (brs, 1H), δ=10.3 (brs, 1H),

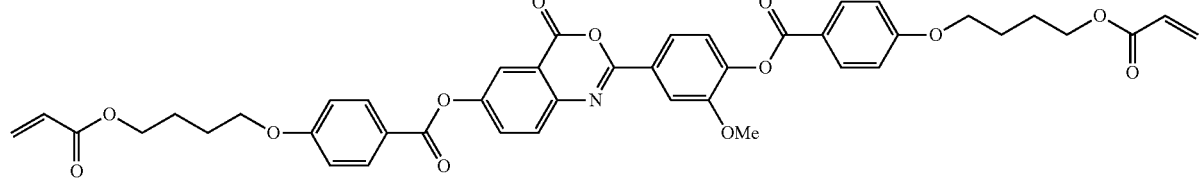

(I-3)

Synthesis of Compound (I-3)

The compound was synthesized using the same method as in Example 1 except that Compound (I-3A) was used instead of Compound (I-1A). The yield was 1.49 g (percentage yield 78%).

1H-NMR (CDCl$_3$): δ=1.8-2.0 (m, 8H), 3.97 (s, 3H), 4.0-4.2 (m, 4H), 4.2-4.3 (m, 4H), 5.83 (d, 2H), 6.12 (dd, 2H), 6.42 (d, 2H), 6.95-7.05 (m, 4H), 7.30 (d, 1H), 7.70 (dd, 1H), 7.77 (d, 1H), 7.94 (d, 1H), 7.99 (dd, 1H), 8.09 (d, 1H), 8.16 (m, 2H), 8.18 (m, 2H)

Example 3

Synthesis of Compound (I-31)

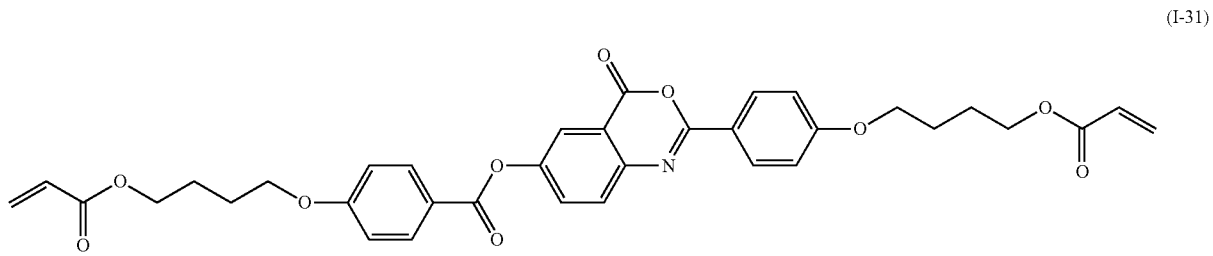 [SMILES: C=CC(=O)OCCCCOc1ccc(C(=O)Oc2ccc3nc(-c4ccc(OCCCCOC(=O)C=C)cc4)oc(=O)c3c2)cc1]

(I-31)

Thionyl chloride (4.4 ml, 61.0 mmol) was added dropwise to a suspension obtained by adding 4-acryloylbutoxybenzoic acid (15.0 g, 56.8 mmol) to tetrahydrofuran (30 ml) and N,N-dimethyl formamide (500 μl), and the resulting solution was stirred as it was at room temperature for 1 hour. The solution obtained above was cooled to 10° C., DIPEA (22.6 ml, 130 mmol) and DMAP (0.2 g) were added, a solution obtained by dissolving 4-hydroxyanthranilic acid (2.49 g, 16.2 mmol) in N-ethyl pyrrolidone (15 ml) was added dropwise, and the resulting solution was stirred at room temperature for 2 hours. Ethyl acetate (150 ml) was added to a reaction fluid, the solution was separated twice using an aqueous solution of 0.5 mol/L hydrochloric acid (150 ml), and the solvent was removed under reduced pressure. An obtained residue was purified through silica gel chromatography, thereby obtaining Compound (I-31) (6.51 g, percentage yield 64%) which is a white solid.

1H-NMR (CDCl$_3$): δ=1.8-2.0 (m, 8H), 4.0-4.2 (m, 4H), 4.2-4.3 (m, 4H), 5.83 (d, 2H), 6.12 (dd, 2H), 6.40 (d, 2H), 6.95-7.05 (m, 4H), 7.67 (dd, 1H), 7.70 (d, 1H), 8.03 (d, 1H), 8.17 (m, 2H), 8.25 (m, 2H)

Example 4

Synthesis of Compound (I-39)

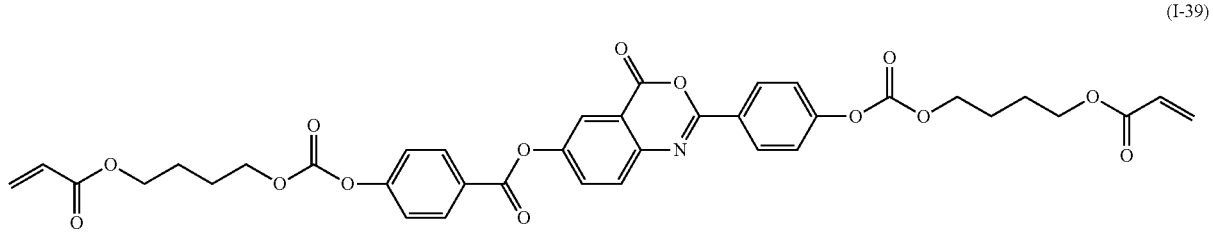 [SMILES: C=CC(=O)OCCCCOC(=O)Oc1ccc(C(=O)Oc2ccc3nc(-c4ccc(OC(=O)OCCCCOC(=O)C=C)cc4)oc(=O)c3c2)cc1]

(I-39)

The compound was synthesized using the same method as in Example 3 except that 4-acryloylbutoxycarbonyloxy benzoic acid was used instead of 4-acryloylbutoxybenzoic acid. The yield was 3.6 g (percentage yield 65%).

1H-NMR (CDCl$_3$): δ=1.8-2.0 (m, 8H), 4.0-4.2 (m, 4H), 4.2-4.3 (m, 4H), 5.83 (d, 2H), 6.12 (dd, 2H), 6.40 (d, 2H), 7.3-7.4 (m, 4H), 7.67 (dd, 1H), 7.70 (d, 1H), 8.03 (d, 1H), 8.2-8.3 (m, 4H)

(Evaluation of the Physical Properties of the Compound)

The Δn of the respective compounds synthesized in Examples 1 to 4 was directly measured according to the method described on p. 202 of Liquid Crystal Handbook (by The liquid crystal handbook editing committee). Specifically, each of the compounds synthesized in Examples 1 to 4 was injected into a wedge-type cell, laser light having a wavelength of 550 nm was radiated on the compound, and the refraction angle of transmitted light was measured, thereby obtaining a Δn. In addition, the phase transition temperature was obtained through texture observation using a polarization microscope, and the coloring of crystals was visually checked. The same measurement and checking were carried out on the following comparative compounds (R-1), (R-2) and (R-3). (R-1) is a monoazomethine compound, (R-2) is a bis azomethine compound and (R-3) is a liquid crystalline compound not including an azomethine group.

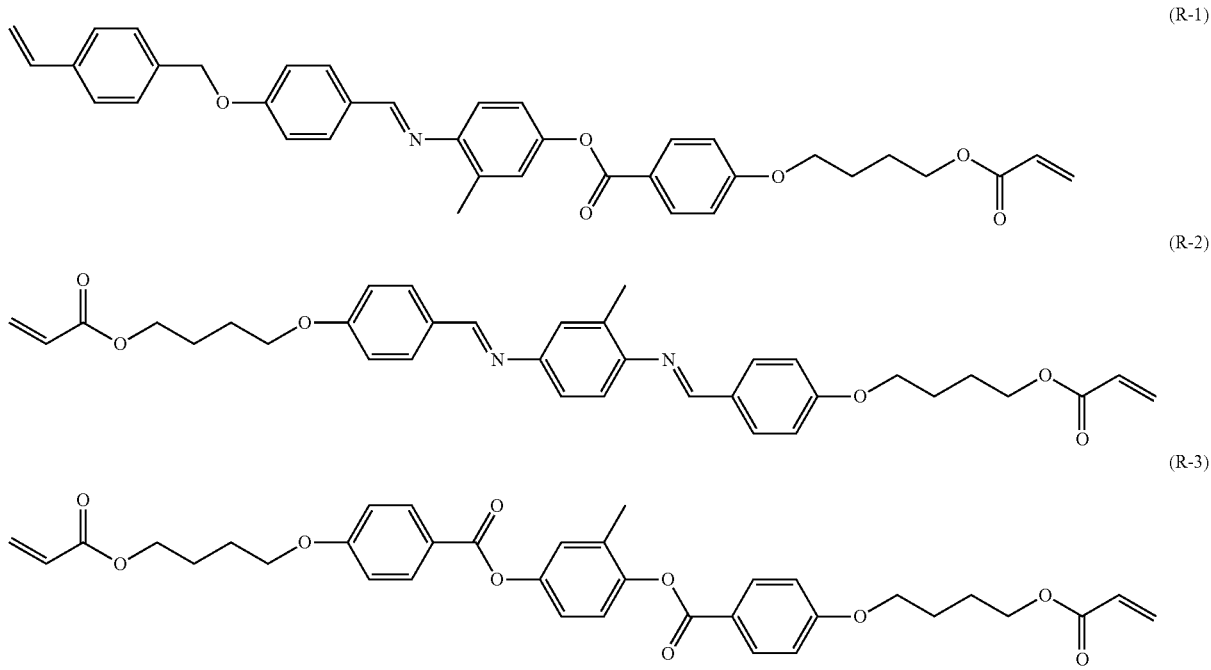

The results of the above measurement and observation are described in the following table. Meanwhile, the temperature in parentheses in the column of "Δn" in the following table refers to the measurement temperature.

TABLE 1

| | Compound used | Phase transition temperature | Δn (measurement temperature) | Color |
|---|---|---|---|---|
| Example 1 | Compound (I-1) | Cr 102 Sc 137 N 240 degrees or higher Iso | 0.270 (70° C.) | White |
| Example 2 | Compound (I-3) | Cr 90 N 240 degrees or higher Iso | 0.268 (70° C.) | White |
| Example 3 | Compound (I-31) | Cr 106 N 173 degrees or higher Iso | 0.256 (70° C.) | White |
| Example 4 | Compound (I-39) | Cr 95 N 175 Iso | 0.253 (70° C.) | White |
| Comparative Example 1 | Compound (R-1) | Cr 77 N 118 Iso | 0.239 (70° C.) | White |
| Comparative Example 2 | Compound (R-2) | Cr 79 N 145 Iso | 0.319 (70° C.) | Yellow |
| Comparative Example 3 | Compound (R-3) | Cr 80 N 124 Iso | 0.162 (70° C.) | White |

From the results described in the above table, it can be understood that, compared with the monoazomethine-type polymerizable liquid crystalline compound (R-1) outside the range of the compound (I) and the liquid crystalline compound (R-3) not including an azomethine group, the compounds of the formula (I) all have a high Δn. In addition, from the absorption spectrum curves illustrated in FIG. 1, it can be understood that the bisazomethine-type polymerizable liquid crystalline compound (R-2), which has been known in the past, absorbs light at a wavelength of 400 nm or more so as to have a yellow color, but the azomethine compound of the formula (I) of the invention slightly absorbs light at a wavelength of 400 nm or more, and is white.

2. Production and Evaluation of Phase Difference Films

Example 5

A liquid crystalline composition coating fluid having the following composition was prepared using Compound (I-1) of the invention synthesized in Example 1.

| | |
|---|---|
| Compound (I-1) | 100 parts by mass |
| Air interface orientation agent (1) | 0.1 parts by mass |
| Polymerization initiator IRGACURE 819 (manufactured by Ciba Japan K.K.) | 3 parts by mass |
| Solvent: chloroform | 800 parts by mass |

-continued

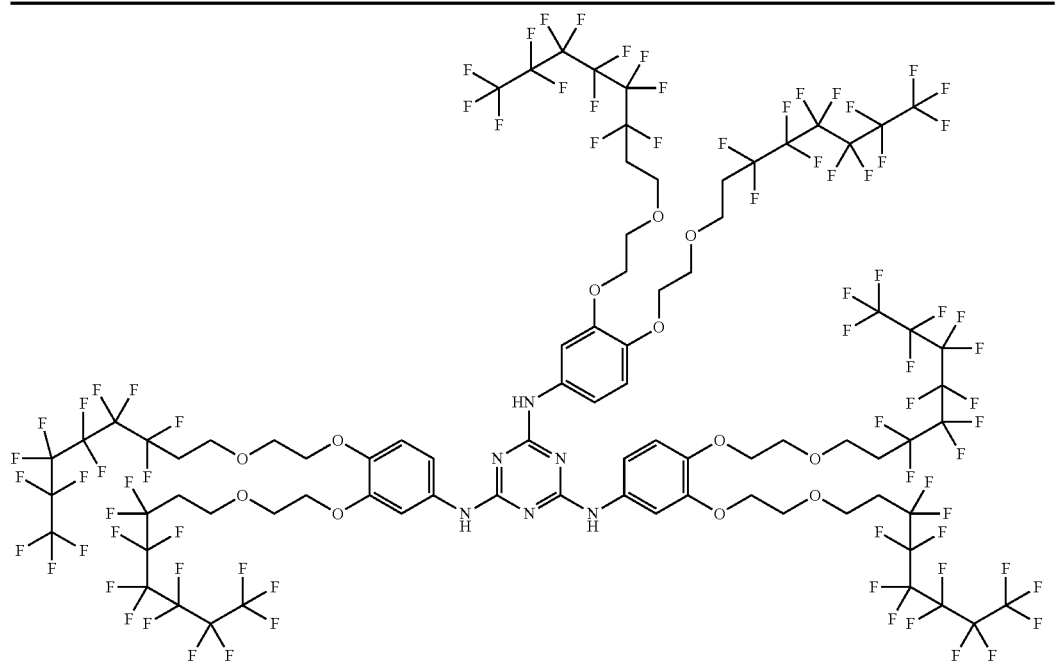

Air interface orientation agent (1)

Next, a polyimide oriented film SE-130 manufactured by Nissan Chemical Industries, Ltd. was coated on a washed glass substrate using a spin coating method, dried, and then fired at 250° C. for 1 hour. A rubbing treatment was carried out on the substrate, thereby producing an orientation film-attached substrate. The liquid crystalline composition coating fluid was coated on the rubbing-treated surface of the oriented film on the substrate at room temperature using a spin coating method, the orientation was aged at 110° C. for 30 seconds, and then light was radiated for 10 seconds using a high-pressure mercury lamp from which a short-wavelength component of UV had been removed at room temperature in a nitrogen gas atmosphere so as to fix the orientation, thereby producing the phase difference film of Example 5. There were no crystals precipitated in the coated film after coating until heating.

As a result of observing the phase difference film obtained by orientating and fixing the liquid crystalline composition using a polarization microscope, it could be confirmed that there were no orientation defects and the film was uniformly uniaxially oriented.

Furthermore, as a result of measuring the film in a Tip-Tilt mode using an AxoScan manufactured by AXOMETRIX Inc., the average inclination angle of the liquid crystal, which was computed using the above apparatus, was 1 degree, and an A-plate-type phase difference film was formed.

In addition, the $\Delta$n at a wavelength of 550 nm, which was computed from a phase difference measured using the above apparatus and a film thickness of the phase difference film measured using a confocal laser film thickness measuring device (FV-7510 manufactured by Keyence Corporation) was 0.258.

In order to check the light resistance, ultraviolet rays of 400 W/m$^2$ with wavelengths of 360 nm or less cut out were radiated on the film for 1000 hours using a xenon lamp. After that, the $\Delta$n at a wavelength of 550 nm was measured before and after the radiation of ultraviolet rays using an AxoScan manufactured by AXOMETRIX Inc., and was 0.257. A $\Delta$n change rate was computed from $\Delta n^a$ before the radiation and $\Delta n^b$ after the radiation using a formula of $(\Delta n^a - \Delta n^b)/\Delta n^a$, and was 0.004.

In addition, in order to check the hydrolysis resistance, a hydrolysis acceleration test was carried out on the phase difference film obtained through the above operations under conditions of 60° C. and a relative humidity of 80% for 168 hours, and the presence of a change of the phase difference film into yellow was checked.

Examples 6 to 8

Liquid crystalline composition coating fluids were prepared respectively in the same manner except that the respective compounds respectively synthesized in Examples 2 to 4 were used instead of Compound (I-1). Phase difference films of the respective examples were formed respectively in the same manner as in Example 5 using the coating fluids respectively.

For the phase difference films as well, the $\Delta$n of the phase difference films, the presence of coloring after aging in a hot and humid environment and the change amount of $\Delta$n after the radiation of ultraviolet rays for 1000 hours, which were obtained in the same manner as in Example 5, were summarized in the following table.

Comparative Examples 4 to 6

Liquid crystalline composition coating fluids were respectively prepared in the same manner except that Comparative Compounds (R-1), (R-2) and (R-3) were used respectively instead of Compound (I-1). Phase difference films of the respective examples were respectively formed in the same manner as in Example 5 using the coating fluids respectively.

For the phase difference films as well, the $\Delta$n of the phase difference films, the presence of coloring after aging in a hot and humid environment and the change amount of $\Delta$n after the radiation of ultraviolet rays for 1000 hours, which were obtained in the same manner as in Example 5, were summarized in the following table.

The results are described in the following table.

TABLE 2

| | Compound used | Δn | Coloring after being aged in a hot and humid environment | Light resistance Δn change rate |
|---|---|---|---|---|
| Example 5 | Compound (I-1) | 0.258 | ○ | 0.004 |
| Example 6 | Compound (I-3) | 0.256 | ○ | 0.005 |
| Example 7 | Compound (I-31) | 0.254 | ○ | 0.006 |
| Example 8 | Compound (I-39) | 0.246 | ○ | 0.005 |
| Comparative Example 4 | Compound (R-1) | 0.244 | X changed to be yellow | 0.087 |
| Comparative Example 5 | Compound (R-2) | 0.291 | X Yellow | 0.181 |
| Comparative Example 6 | Compound (R-3) | 0.160 | ○ | 0.002 |

From the results described in the above table, it can be understood that the phase difference film produced using the compound of the formula (I) of the invention has a large Δn and is excellent in terms of hydrolysis resistance and light resistance compared with a phase difference film produced using the monoazomethine-type polymerizable liquid crystalline compound (R-1) of the related art. In addition, it can be understood that, while the film produced using the bisazomethine-type polymerizable liquid crystalline compound (R-2) of the related art is yellow, the phase difference films of the examples of the invention are all white and excellent in terms of hydrolysis resistance and light resistance. In addition, it can be understood that, compared with the liquid crystalline compound (R-3) not including an azomethine group, the compounds of the formula (I) all have a high Δn.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2012/056502, filed Mar. 14, 2012; and Japanese Application No. 2011-058442, filed Mar. 16, 2011, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A compound which has a benzoxazinone ring and an aromatic ring that directly bonds to the benzoxazinone ring, and has a mesogenic core substituted by a substituent having a polymerizable functional group, which is represented by the following formula (I):

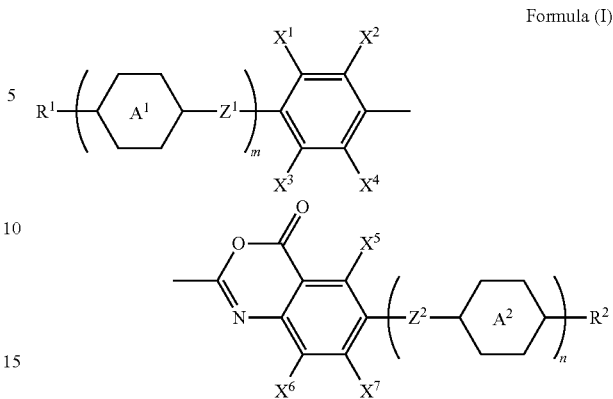

Formula (I)

wherein each of $R^1$ and $R^2$ independently represents a hydrogen atom, a halogen, $NO_2$, CN, NCS, a linear, branched or cyclic alkyl group having 1 to 12 carbon atoms (here, among —$CH_2$— that configure the alkyl group, one —$CH_2$— or two or more non-adjacent —$CH_2$— may be substituted by —O—, —S—, —CO—, —COO—, —OCO—, —OCOO—, —CH=CH—, —C≡C—, —$CONR^3$—, —$NR^3CO$— or —$NR^3$—) or P-Sp-L-, and at least one of $R^1$ and $R^2$ is P-Sp-L-;

P represents a polymerizable functional group;

Sp represents a single bond or an alkylene group having 1 to 12 carbon atoms (here, among non-terminal —$CH_2$— that configure the alkylene group, one non-terminal —$CH_2$— or two or more non-adjacent non-terminal —$CH_2$— may be substituted by —O—, —S—, —CO—, —COO—, —OCO—, —CH=CH—, —C≡C—, —$CONR^4$—, —$NR^4CO$— or —$NR^4$—);

L represents —O—, —S—, —CO—, —COO—, —OCO—, —OCOO—, —$CONR^5$—, —$NR^5CO$—, —$NR^5$— or a single bond; when Sp is a single bond, L is also a single bond;

each of $A^1$ and $A^2$ independently represents a 1,4-phenylene group; one or two or more hydrogen atoms in the 1,4-phenylene group may be substituted by an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $Z^1$ and $Z^2$ independently represents —COO—, —OCO—, —$CONR^6$—, —$NR^6CO$—, —$OCH_2$—, —$CH_2O$—, —$CH_2S$—, —$SCH_2$—, —$CH_2CH_2$— or a single bond;

each of $X^1$, $X^2$, $X^3$, $X^4$, $X^5$, $X^6$ and $X^7$ independently represents a hydrogen atom, an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $R^3$, $R^4$, $R^5$ and $R^6$ independently represents a hydrogen atom or an alkyl group having 1 to 4 carbon atoms;

each of m and n independently represents 0, 1 or 2, and m+n=1 or 2.

2. The compound according to claim 1, wherein, in the formula (I), when m=n=1, $Z^1$ is —COO—, and $Z^2$ is —OCO—.

3. The compound according to claim 2, wherein, in the formula (I), $X^3$ is a hydrogen atom or a methoxy group.

4. The compound according to claim 1, wherein, in the formula (I), when m=0 and n=1, $Z^2$ is —OCO—.

5. The compound according to claim 1, wherein, in the formula (I), when m=1 and n=0, $Z^1$ is —COO—.

6. The compound according to claim 1, wherein, in the formula (I), P is a methacrylate group, an acrylate group, an alicyclic ether group, a cyclic acetal group, a cyclic lactone group, a cyclic thioether group, a spiro ortho ester group or a vinyloxy group.

7. The compound according to claim 1, wherein, in the formula (I), P is a polymerizable functional group selected from a group consisting of groups represented by the following formulae (P-1) to (P-5):

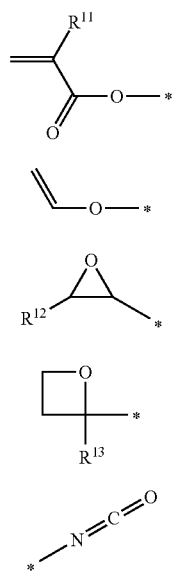

wherein, in the formulae, each of $R^{11}$ to $R^{13}$ independently represents a hydrogen atom or a methyl group.

8. The compound according to claim 1, wherein, in the formula (I), P is a methacrylate group or an acrylate group.

9. The compound according to claim 1, wherein, in the formula (I), Sp is an alkylene group having 2 to 8 carbon atoms.

10. The compound according to claim 1, wherein, in the formula (I), Sp is an alkylene group having 3 to 6 carbon atoms.

11. The compound according to claim 1, wherein, in the formula (I), each of $R^1$ and $R^2$ is a linear, branched or cyclic alkyl group having 1 to 12 carbon atoms in which one $CH_2$ or two or more non-adjacent $CH_2$ may be substituted by —O— or —OCOO—, or P-Sp-L-.

12. The compound according to claim 1, wherein, in the formula (I), $R^1$ and $R^2$ are a group represented by P-Sp-L-.

13. The compound according to claim 1, wherein, in the formula (I), L is —O— or —OCOO—.

14. The compound according to claim 1, wherein, in the formula (I), each of $Z^1$ and $Z^2$ is —COO— or —OCO—.

15. The compound according to claim 1, wherein, in the formula (I), each of $X^1$, $X^2$, $X^3$, $X^4$, $X^5$, $X^6$ and $X^7$ is a hydrogen atom, an alkyl group having 1 or 2 carbon atoms, an alkoxy group having 1 or 2 carbon atoms or a halogen atom.

16. The compound according to claim 1, wherein, in the formula (I), each of $X^1$, $X^2$, $X^3$, $X^4$, $X^5$, $X^6$ and $X^7$ is a hydrogen atom, a methyl group, a methoxy group or a chlorine atom.

17. A polymerizable liquid crystalline composition containing a compound and a chiral agent, wherein the compound has a benzoxazinone ring and an aromatic ring that directly bonds to the benzoxazinone ring, and has a mesogenic core substituted by a substituent having a polymerizable functional group, wherein the compound is represented by the following formula (I):

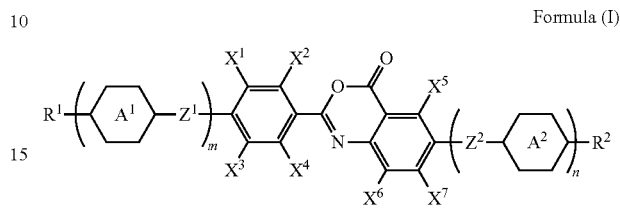

Formula (I)

wherein each of $R^1$ and $R^2$ independently represents a hydrogen atom, a halogen, $NO_2$, CN, NCS, a linear, branched or cyclic alkyl group having 1 to 12 carbon atoms (here, among —$CH_2$— that configure the alkyl group, one —$CH_2$— or two or more non-adjacent —$CH_2$— may be substituted by —O—, —S—, —CO—, —COO—, —OCO—, —OCOO—, —CH=CH—, —C≡C—, —$CONR^3$—, —$NR^3CO$— or —$NR^3$—) or P-Sp-L-, and at least one of $R^1$ and $R^2$ is P-Sp-L-;

P represents a polymerizable functional group;

Sp represents a single bond or an alkylene group having 1 to 12 carbon atoms (here, among non-terminal —$CH_2$— that configure the alkylene group, one non-terminal —$CH_2$— or two or more non-adjacent non-terminal —$CH_2$— may be substituted by —O—, —S—, —CO—, —COO—, —OCO—, —CH=CH—, —C≡C—, —$CONR^4$—, —$NR^4CO$— or —$NR^4$—);

L represents —O—, —S—, —CO—, —COO—, —OCO—, —OCOO—, —$CONR^5$—, —$NR^5CO$—, —$NR^5$— or a single bond; when Sp is a single bond, L is also a single bond;

each of $A^1$ and $A^2$ independently represents a 1,4-phenylene group; one or two or more hydrogen atoms in the 1,4-phenylene group may be substituted by an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $Z^1$ and $Z^2$ independently represents —COO—, —OCO—, —$CONR^6$—, —$NR^6CO$—, —$OCH_2$—, —$CH_2O$—, —$CH_2S$—, —$SCH_2$—, —$CH_2CH_2$— or a single bond;

each of $X^1$, $X^2$, $X^3$, $X^4$, $X^5$, $X^6$ and $X^7$ independently represents a hydrogen atom, an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $R^3$, $R^4$, $R^5$ and $R^6$ independently represents a hydrogen atom or an alkyl group having 1 to 4 carbon atoms;

each of m and n independently represents 0, 1 or 2, and m+n=1 or 2.

18. A macromolecular compound obtained by polymerizing a compound which has a benzoxazinone ring and an aromatic ring that directly bonds to the benzoxazinone ring, and has a mesogenic core substituted by a substituent having a polymerizable functional group, wherein the compound is represented by the following formula (I):

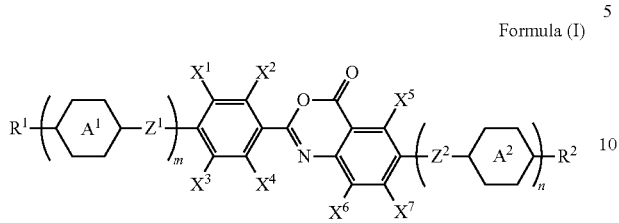

Formula (I)

wherein each of $R^1$ and $R^2$ independently represents a hydrogen atom, a halogen, NO, CN, NCS, a linear, branched or cyclic alkyl group having 1 to 12 carbon atoms (here, among —$CH_2$— that configure the alkyl group, one —$CH_2$— or two or more non-adjacent —$CH_2$— may be substituted by —O—, —S—, —CO—, —COO—, —OCO—, —OCOO—, —CH=CH—, —C≡C—, —$CONR^3$—, —$NR^3CO$— or —$NR^3$—) or P-Sp-L-, and at least one of $R^1$ and $R^2$ is P-Sp-L-;

P represents a polymerizable functional group;

Sp represents a single bond or an alkylene group having 1 to 12 carbon atoms (here, among non-terminal —$CH_2$— that configure the alkylene group, one non-terminal —$CH_2$— or two or more non-adjacent non-terminal —$CH_2$— may be substituted by —O—, —S—, —CO—, —COO—, —OCO—, —CH=CH—, —C≡C—, —$CONR^4$—, —$NR^4CO$— or —$NR^4$—);

L represents —O—, —S—, —CO—, —COO—, —OCO—, —OCOO—, —$CONR^5$—, —$NR^5CO$—, —$NR^5$— or a single bond; when Sp is a single bond, L is also a single bond;

each of $A^1$ and $A^2$ independently represents a 1,4-phenylene group; one or two or more hydrogen atoms in the 1,4-phenylene group may be substituted by an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $Z^1$ and $Z^2$ independently represents —COO—, —OCO—, —$CONR^6$—, —$NR^6CO$—, —$OCH_2$—, —$CH_2O$—, —$CH_2S$—, —$SCH_2$—, —$CH_2CH_2$— or a single bond;

each of $X^1$, $X^2$, $X^3$, $X^4$, $X^5$, $X^6$ and $X^7$ independently represents a hydrogen atom, an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $R^3$, $R^4$, $R^5$ and $R^6$ independently represents a hydrogen atom or an alkyl group having 1 to 4 carbon atoms;

each of m and n independently represents 0, 1 or 2, and m+n=1 or 2.

19. A film using a compound which has a benzoxazinone ring and an aromatic ring that directly bonds to the benzoxazinone ring, and has a mesogenic core substituted by a substituent having a polymerizable functional group, wherein the compound is represented by the following formula (I):

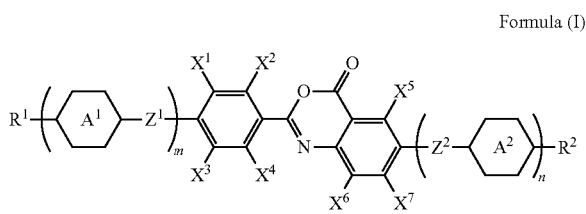

Formula (I)

wherein each of $R^1$ and $R^2$ independently represents a hydrogen atom, a halogen, $NO_2$, CN, NCS, a linear, branched or cyclic alkyl group having 1 to 12 carbon atoms (here, among —$CH_2$— that configure the alkyl group, one —$CH_2$— or two or more non-adjacent —$CH_2$— may be substituted by —O—, —S—, —CO—, —COO—, —OCO—, —OCOO—, —CH=CH—, —C≡C—, —$CONR^3$—, —$NR^3CO$— or —$NR^3$—) or P-Sp-L-, and at least one of $R^1$ and $R^2$ is P-Sp-L-;

P represents a polymerizable functional group;

Sp represents a single bond or an alkylene group having 1 to 12 carbon atoms (here, among non-terminal —$CH_2$— that configure the alkylene group, one non-terminal —$CH_2$— or two or more non-adjacent non-terminal —$CH_2$— may be substituted by —O—, —S—, —CO—, —COO—, —OCO—, —CH=CH—, —C≡C—, —$CONR^4$—, —$NR^4CO$— or —$NR^4$—);

L represents —O—, —S—, —CO—, —COO—, —OCO—, —OCOO—, —$CONR^5$—, —$NR^5CO$—, —$NR^5$— or a single bond; when Sp is a single bond, L is also a single bond;

each of $A^1$ and $A^2$ independently represents a 1,4-phenylene group; one or two or more hydrogen atoms in the 1,4-phenylene group may be substituted by an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $Z^1$ and $Z^2$ independently represents —COO—, —OCO—, —$CONR^6$—, —$NR^6CO$—, —$OCH_2$—, —$CH_2O$—, —$CH_2S$—, —$SCH_2$—, —$CH_2CH_2$— or a single bond;

each of $X^1$, $X^2$, $X^3$, $X^4$, $X^5$, $X^6$ and $X^7$ independently represents a hydrogen atom, an alkyl group having 1 to 4 carbon atoms, an alkoxy group having 1 to 4 carbon atoms, an alkoxycarbonyl group having 2 to 5 carbon atoms, an acyloxy group having 2 to 5 carbon atoms, an acyl group having 2 to 4 carbon atoms, an amide group having 2 to 5 carbon atoms, a cyano group or a halogen atom;

each of $R^3$, $R^4$, $R^5$ and $R^6$ independently represents a hydrogen atom or an alkyl group having 1 to 4 carbon atoms;

each of m and n independently represents 0, 1 or 2, and m+n=1 or 2.

\* \* \* \* \*